(12) United States Patent
Li et al.

(10) Patent No.: US 11,147,500 B2
(45) Date of Patent: *Oct. 19, 2021

(54) ELECTROCARDIOGRAM PROCESSING SYSTEM FOR DELINEATION AND CLASSIFICATION

(71) Applicant: Cardiologs Technologies SAS, Paris (FR)

(72) Inventors: Jia Li, Paris (FR); Romain Pomier, Paris (FR); Chiara Scabellone, Paris (FR); Cyril Gaudefroy, Paris (FR); Benjamin Barre, Suresnes (FR); Julien Fontanarava, Paris (FR); Christophe Gardella, Paris (FR); Mathieu Sornay, Paris (FR); Thomas Bordier, Paris (FR)

(73) Assignee: Cardiologs Technologies SAS, Paris (FR)

(*) Notice: Subject to any disclaimer, the term of this patent is extended or adjusted under 35 U.S.C. 154(b) by 0 days.

This patent is subject to a terminal disclaimer.

(21) Appl. No.: 17/209,129

(22) Filed: Mar. 22, 2021

(65) Prior Publication Data

US 2021/0204860 A1 Jul. 8, 2021

Related U.S. Application Data

(63) Continuation of application No. 16/267,380, filed on Feb. 4, 2019, now Pat. No. 10,959,660, which is a
(Continued)

(30) Foreign Application Priority Data

Oct. 27, 2015 (EP) .................................. 15191769

(51) Int. Cl.
*A61B 5/361* (2021.01)
*G16H 50/30* (2018.01)
(Continued)

(52) U.S. Cl.
CPC .............. *A61B 5/361* (2021.01); *A61B 5/316* (2021.01); *A61B 5/349* (2021.01); *A61B 5/364* (2021.01);
(Continued)

(58) Field of Classification Search
CPC ....... A61B 5/361; A61B 5/366; A61B 5/7264; A61B 5/364; A61B 5/316; A61B 5/349;
(Continued)

(56) References Cited

U.S. PATENT DOCUMENTS

| | | | |
|---|---|---|---|
| 5,024,225 A | 6/1991 | Fang | |
| 5,239,494 A | 8/1993 | Golbeck | |

(Continued)

FOREIGN PATENT DOCUMENTS

| | | |
|---|---|---|
| CA | 2466848 A1 | 6/2003 |
| CA | 2975610 A1 | 8/2016 |

(Continued)

OTHER PUBLICATIONS

Alfonso, et al., ECG Beat Detection Using Filter Banks, *IEEE Transactions on Biomedical Engineering*, 46(2):192-202 (Feb. 1999).

(Continued)

*Primary Examiner* — Mark W. Bockelman
(74) *Attorney, Agent, or Firm* — Eversheds Sutherland (US) LLP; Christopher C. Bolten; Robert D. Ward

(57) ABSTRACT

Systems and methods are provided for analyzing electrocardiogram (ECG) data of a patient using a substantial amount of ECG data. The systems receive ECG data from a sensing device positioned on a patient such as one or more ECG leads. The system may include an application that communicates with an ECG platform running on a server(s) that processes and analyzes the ECG data, e.g., using neural networks for delineation of the cardiac signal and classification of various abnormalities, conditions and/or descrip- (Continued)

tors. The processed ECG data is communicated from the server(s) for display in a user-friendly and interactive manner with enhanced accuracy.

30 Claims, 24 Drawing Sheets

Related U.S. Application Data continuation-in-part of application No. PCT/EP2018/072912, filed on Aug. 24, 2018, and a continuation-in-part of application No. 15/771,807, filed as application No. PCT/EP2016/075972 on Oct. 27, 2016, now Pat. No. 10,779,744, which is a continuation-in-part of application No. 14/924,239, filed on Oct. 27, 2015, now Pat. No. 10,426,364.

(60) Provisional application No. 62/549,994, filed on Aug. 25, 2017.

(51) Int. Cl.
| | |
|---|---|
| *G16H 50/20* | (2018.01) |
| *A61B 5/366* | (2021.01) |
| *A61B 5/316* | (2021.01) |
| *A61B 5/00* | (2006.01) |
| *A61B 5/364* | (2021.01) |
| *A61B 5/349* | (2021.01) |

(52) U.S. Cl.
CPC ............ *A61B 5/366* (2021.01); *A61B 5/7264* (2013.01); *G16H 50/20* (2018.01); *G16H 50/30* (2018.01); *A61B 5/7203* (2013.01); *A61B 5/7221* (2013.01); *A61B 5/7267* (2013.01); *A61B 5/7282* (2013.01)

(58) Field of Classification Search
CPC ... A61B 5/7267; A61B 5/7203; A61B 5/7221; A61B 5/7282; G16H 50/20; G16H 50/30
See application file for complete search history.

(56) References Cited

U.S. PATENT DOCUMENTS

| | | | |
|---|---|---|---|
| 5,619,991 | A | 4/1997 | Sloane |
| 5,623,935 | A | 4/1997 | Faisandier |
| 5,819,007 | A | 10/1998 | Elghazzawi |
| 5,907,291 | A | 5/1999 | Chen et al. |
| 5,966,692 | A | 10/1999 | Langer et al. |
| 6,024,699 | A | 2/2000 | Surwit et al. |
| 6,157,850 | A | 12/2000 | Diab et al. |
| 6,507,753 | B1 | 1/2003 | Xue et al. |
| 6,612,985 | B2 | 9/2003 | Eiffert et al. |
| 6,656,125 | B2 | 12/2003 | Misczynski et al. |
| 6,694,177 | B2 | 2/2004 | Eggers et al. |
| 7,142,907 | B2 | 11/2006 | Xue et al. |
| 7,289,844 | B2 | 10/2007 | Misczynski et al. |
| 7,941,207 | B2 | 5/2011 | Korzinov |
| RE43,767 | E | 10/2012 | Eggers et al. |
| 8,332,017 | B2 | 12/2012 | Tarassenko et al. |
| 8,668,644 | B2 | 3/2014 | Ong et al. |
| 8,818,496 | B2 | 8/2014 | Dziubinski et al. |
| D717,955 | S | 11/2014 | Bishay et al. |
| 8,903,479 | B2 | 12/2014 | Zoicas |
| 8,932,220 | B2 | 1/2015 | Ong et al. |
| 8,951,193 | B2 | 2/2015 | Ong et al. |
| D744,659 | S | 12/2015 | Bishay et al. |
| 9,241,650 | B2 | 1/2016 | Amirim |
| 9,254,095 | B2 | 2/2016 | Galloway et al. |
| 9,295,429 | B2 | 3/2016 | Ong et al. |
| 9,339,202 | B2 | 5/2016 | Brockway et al. |
| 9,345,414 | B1 | 5/2016 | Bardy et al. |
| 9,351,652 | B2 | 5/2016 | Dziubinski et al. |
| 9,364,155 | B2 | 6/2016 | Bardy et al. |
| 9,408,545 | B2 | 8/2016 | Felix et al. |
| 9,408,551 | B2 | 8/2016 | Bardy et al. |
| 9,420,957 | B2 | 8/2016 | Ong |
| D766,447 | S | 9/2016 | Bishay et al. |
| 9,433,367 | B2 | 9/2016 | Felix et al. |
| 9,433,380 | B1 | 9/2016 | Bishay et al. |
| 9,468,386 | B2 | 10/2016 | Braojos Lopez et al. |
| 9,504,423 | B1 | 11/2016 | Bardy et al. |
| 9,545,204 | B2 | 1/2017 | Bishay et al. |
| 9,545,228 | B2 | 1/2017 | Bardy et al. |
| 9,554,715 | B2 | 1/2017 | Bardy et al. |
| 9,615,763 | B2 | 4/2017 | Felix et al. |
| 9,619,660 | B1 | 4/2017 | Felix et al. |
| 9,642,537 | B2 | 5/2017 | Felix et al. |
| 9,655,537 | B2 | 5/2017 | Bardy et al. |
| 9,655,538 | B2 | 5/2017 | Felix et al. |
| 9,700,227 | B2 | 7/2017 | Bishay et al. |
| D793,566 | S | 8/2017 | Bishay et al. |
| 9,717,432 | B2 | 8/2017 | Felix et al. |
| 9,717,433 | B2 | 8/2017 | Felix et al. |
| 9,730,593 | B2 | 8/2017 | Felix et al. |
| 9,730,641 | B2 | 8/2017 | Felix et al. |
| 9,737,211 | B2 | 8/2017 | Bardy et al. |
| 9,737,224 | B2 | 8/2017 | Bardy et al. |
| D801,528 | S | 10/2017 | Bardy et al. |
| 9,775,536 | B2 | 10/2017 | Felix et al. |
| 9,788,722 | B2 | 10/2017 | Bardy et al. |
| 9,808,206 | B1 | 11/2017 | Zhao et al. |
| 9,820,665 | B2 | 11/2017 | Felix et al. |
| 9,901,274 | B2 | 2/2018 | Bishay et al. |
| 9,936,875 | B2 | 4/2018 | Bardy et al. |
| 9,955,885 | B2 | 5/2018 | Felix et al. |
| 9,955,888 | B2 | 5/2018 | Felix et al. |
| 9,955,911 | B2 | 5/2018 | Bardy et al. |
| 10,004,415 | B2 | 6/2018 | Bishay et al. |
| 10,045,709 | B2 | 8/2018 | Bardy et al. |
| 10,052,022 | B2 | 8/2018 | Bardy et al. |
| D831,833 | S | 10/2018 | Bishay et al. |
| 10,111,601 | B2 | 10/2018 | Bishay et al. |
| 10,123,703 | B2 | 11/2018 | Bardy et al. |
| 10,154,793 | B2 | 12/2018 | Felix et al. |
| D838,370 | S | 1/2019 | Bardy et al. |
| 10,165,946 | B2 | 1/2019 | Bardy et al. |
| 10,172,534 | B2 | 1/2019 | Felix et al. |
| 10,251,575 | B2 | 4/2019 | Bardy et al. |
| 10,251,576 | B2 | 4/2019 | Bardy et al. |
| 10,264,992 | B2 | 4/2019 | Felix et al. |
| 10,265,015 | B2 | 4/2019 | Bardy et al. |
| 10,271,755 | B2 | 4/2019 | Felix et al. |
| 10,271,756 | B2 | 4/2019 | Felix et al. |
| 10,278,603 | B2 | 5/2019 | Felix et al. |
| 10,278,606 | B2 | 5/2019 | Bishay et al. |
| 10,426,364 | B2 | 10/2019 | Rapin et al. |
| 10,492,730 | B1 | 12/2019 | Mehta |
| 10,959,660 | B2 * | 3/2021 | Li ..................... A61B 5/366 |
| 2001/0029338 | A1 | 10/2001 | Krishnamachari |
| 2003/0176795 | A1 | 9/2003 | Harris et al. |
| 2004/0147840 | A1 | 7/2004 | Duggirala et al. |
| 2004/0230105 | A1 | 11/2004 | Geva et al. |
| 2004/0260192 | A1 | 12/2004 | Yamamoto |
| 2005/0101873 | A1 | 5/2005 | Misczynski et al. |
| 2005/0113706 | A1 | 5/2005 | Prystowsky et al. |
| 2005/0171448 | A1 | 8/2005 | Korzinov et al. |
| 2005/0182334 | A1 | 8/2005 | Korzinov et al. |
| 2005/0222508 | A1 | 10/2005 | Moreno et al. |
| 2006/0020219 | A1 | 1/2006 | Zinser, Jr. et al. |
| 2006/0173369 | A1 | 8/2006 | Kaski |
| 2007/0129642 | A1 | 6/2007 | Korzinov |
| 2007/0191723 | A1 | 8/2007 | Prystowsky et al. |
| 2008/0004904 | A1 | 1/2008 | Tran |
| 2008/0082016 | A1 | 4/2008 | Kohls et al. |
| 2008/0103403 | A1 | 5/2008 | Cohen |
| 2008/0132799 | A1 | 6/2008 | Xue |
| 2009/0112110 | A1 | 4/2009 | Zhang |
| 2009/0192394 | A1 | 7/2009 | Guttag et al. |
| 2010/0076331 | A1 | 3/2010 | Chan et al. |
| 2010/0268103 | A1 | 10/2010 | McNamara et al. |
| 2011/0184297 | A1 | 7/2011 | Vitali et al. |

(56) References Cited

U.S. PATENT DOCUMENTS

| | | |
|---|---|---|
| 2011/0224565 A1 | 9/2011 | Ong et al. |
| 2011/0257548 A1 | 10/2011 | Dong et al. |
| 2011/0282225 A1 | 11/2011 | Anderson et al. |
| 2011/0301435 A1 | 12/2011 | Albert et al. |
| 2012/0110226 A1 | 5/2012 | Vlach et al. |
| 2012/0203491 A1 | 8/2012 | Sun et al. |
| 2012/0278099 A1 | 11/2012 | Kelly et al. |
| 2013/0116585 A1 | 5/2013 | Bouguerra |
| 2013/0184599 A1 | 7/2013 | Friedman et al. |
| 2013/0237776 A1 | 9/2013 | Ong et al. |
| 2014/0005988 A1 | 1/2014 | Brockway |
| 2014/0107493 A1 | 4/2014 | Yuen et al. |
| 2014/0128758 A1 | 5/2014 | Galloway et al. |
| 2014/0148714 A1 | 5/2014 | Mamaghanian et al. |
| 2014/0187988 A1 | 7/2014 | Ong et al. |
| 2014/0228665 A1 | 8/2014 | Albert |
| 2014/0275840 A1 | 9/2014 | Osorio |
| 2015/0008802 A1 | 1/2015 | Fukuda |
| 2015/0018702 A1 | 1/2015 | Galloway et al. |
| 2015/0051505 A1 | 2/2015 | Rossi |
| 2015/0088020 A1 | 3/2015 | Dreisbach et al. |
| 2015/0088024 A1 | 3/2015 | Sackellares et al. |
| 2015/0105640 A1 | 4/2015 | Friedman et al. |
| 2015/0119725 A1 | 4/2015 | Martin et al. |
| 2015/0164349 A1 | 6/2015 | Gopalakrishnan et al. |
| 2015/0190067 A1 | 7/2015 | Prystowsky et al. |
| 2015/0248534 A1 | 9/2015 | Krzywicki et al. |
| 2015/0257668 A1 | 9/2015 | Braojos Lopez et al. |
| 2015/0282726 A1 | 10/2015 | Grube et al. |
| 2015/0289112 A1 | 10/2015 | Gilbert et al. |
| 2016/0051157 A1 | 2/2016 | Waydo |
| 2016/0085927 A1 | 3/2016 | Dettinger et al. |
| 2016/0085937 A1 | 3/2016 | Dettinger et al. |
| 2016/0086297 A1 | 3/2016 | Dettinger et al. |
| 2016/0098536 A1 | 4/2016 | Dettinger et al. |
| 2016/0098537 A1 | 4/2016 | Dettinger et al. |
| 2016/0098538 A1 | 4/2016 | Dettinger et al. |
| 2016/0150989 A1 | 6/2016 | Felix et al. |
| 2016/0183827 A1 | 6/2016 | Xue et al. |
| 2016/0183829 A1 | 6/2016 | Friedman et al. |
| 2016/0192853 A1 | 7/2016 | Bardy et al. |
| 2016/0235319 A1 | 8/2016 | Albert |
| 2016/0242665 A1 | 8/2016 | Galloway et al. |
| 2016/0249823 A1 | 9/2016 | Galloway et al. |
| 2016/0262646 A1 | 9/2016 | Bardy et al. |
| 2016/0321430 A1 | 11/2016 | Eckman et al. |
| 2016/0345854 A1 | 12/2016 | Bardy et al. |
| 2016/0345909 A1 | 12/2016 | Felix et al. |
| 2017/0095153 A1 | 4/2017 | Bardy et al. |
| 2017/0098047 A1 | 4/2017 | Young |
| 2017/0105683 A1 | 4/2017 | Xue |
| 2017/0112401 A1 | 4/2017 | Rapin et al. |
| 2017/0135579 A1 | 5/2017 | Bardy et al. |
| 2017/0177811 A1 | 6/2017 | McFarland et al. |
| 2017/0188872 A1 | 7/2017 | Hughes et al. |
| 2017/0238833 A1 | 8/2017 | Felix et al. |
| 2017/0251948 A1 | 9/2017 | Felix et al. |
| 2017/0258358 A1 | 9/2017 | Bishay et al. |
| 2017/0340206 A1 | 11/2017 | Bardy et al. |
| 2017/0340290 A1 | 11/2017 | Felix et al. |
| 2017/0357764 A1 | 12/2017 | Fauss et al. |
| 2017/0367609 A1 | 12/2017 | Bardy et al. |
| 2018/0020939 A1 | 1/2018 | Albert |
| 2018/0028144 A1 | 2/2018 | Chen et al. |
| 2018/0060522 A1 | 3/2018 | Petterson et al. |
| 2018/0146875 A1 | 5/2018 | Friedman et al. |
| 2018/0177423 A1 | 6/2018 | Bishay et al. |
| 2018/0206752 A1 | 7/2018 | Bardy et al. |
| 2018/0242876 A1 | 8/2018 | Hughes et al. |
| 2018/0279956 A1 | 10/2018 | Waydo et al. |
| 2018/0289274 A1 | 10/2018 | Bahney et al. |
| 2018/0296118 A1 | 10/2018 | Bishay et al. |
| 2018/0310892 A1 | 11/2018 | Perschbacher et al. |
| 2018/0344189 A1 | 12/2018 | Dusan |
| 2018/0344191 A1 | 12/2018 | Bardy et al. |
| 2018/0353071 A1 | 12/2018 | Bardy et al. |
| 2018/0368715 A1 | 12/2018 | Xue et al. |
| 2018/0374576 A1 | 12/2018 | Dettinger et al. |
| 2019/0034050 A1 | 1/2019 | Williams et al. |
| 2019/0038149 A1 | 2/2019 | Gopalakrishnan et al. |
| 2019/0059763 A1 | 2/2019 | Shakur et al. |
| 2019/0069794 A1 | 3/2019 | Bardy et al. |
| 2019/0069798 A1 | 3/2019 | Bardy |
| 2019/0069800 A1 | 3/2019 | Bardy et al. |
| 2019/0076023 A1 | 3/2019 | Bardy et al. |
| 2019/0090769 A1 | 3/2019 | Boleyn et al. |
| 2019/0099105 A1 | 4/2019 | Felix et al. |
| 2019/0104951 A1 | 4/2019 | Valys et al. |
| 2019/0104961 A1 | 4/2019 | Felix et al. |
| 2019/0117068 A1 | 4/2019 | Thomson et al. |
| 2019/0117099 A1 | 4/2019 | Bardy et al. |
| 2019/0117107 A1 | 4/2019 | Felix et al. |
| 2019/0133444 A1 | 5/2019 | Bardy et al. |
| 2019/0133483 A1 | 5/2019 | Xue et al. |
| 2019/0133486 A1 | 5/2019 | Felix et al. |
| 2019/0167141 A1 | 6/2019 | Duckert et al. |
| 2019/0223739 A1 | 7/2019 | Rapin et al. |
| 2019/0259496 A1 | 8/2019 | Pemberton et al. |
| 2019/0267139 A1 | 8/2019 | Hutchins et al. |
| 2019/0272920 A1 | 9/2019 | Teplitzky |
| 2019/0274563 A1 | 9/2019 | Soli et al. |
| 2019/0274574 A1 | 9/2019 | Hughes et al. |
| 2019/0282118 A1 | 9/2019 | Kaski |
| 2019/0298204 A1 | 10/2019 | Fontanarava et al. |
| 2019/0357794 A1 | 11/2019 | Bardy et al. |
| 2020/0013507 A1 | 1/2020 | Braun et al. |
| 2020/0015694 A1 | 1/2020 | Rapin et al. |
| 2020/0022591 A1 | 1/2020 | Drakulic et al. |
| 2020/0022604 A1 | 1/2020 | Scabellone et al. |
| 2020/0060563 A1 | 2/2020 | Boleyn et al. |
| 2020/0118673 A1 | 4/2020 | Dettinger et al. |
| 2020/0155025 A1 | 5/2020 | Smith et al. |
| 2020/0178825 A1 | 6/2020 | Lu et al. |
| 2020/0273567 A1 | 8/2020 | Petterson et al. |
| 2020/0289014 A1 | 9/2020 | Park et al. |
| 2020/0289063 A1 | 9/2020 | Mehta |
| 2020/0401684 A1 | 12/2020 | Vath et al. |
| 2021/0000344 A1 | 1/2021 | Dreisbach et al. |

FOREIGN PATENT DOCUMENTS

| | | |
|---|---|---|
| CA | 2978636 A1 | 9/2016 |
| CN | 101268938 A | 9/2008 |
| CN | 101766484 A | 7/2010 |
| CN | 102188240 A | 9/2011 |
| CN | 102379694 A | 3/2012 |
| CN | 102779234 A | 11/2012 |
| CN | 103038772 A | 4/2013 |
| CN | 103110417 A | 5/2013 |
| CN | 103284702 A | 9/2013 |
| CN | 103417209 A | 12/2013 |
| CN | 104463326 A | 3/2015 |
| CN | 104970789 A | 10/2015 |
| CN | 106778685 A | 5/2017 |
| DE | 60127354 T2 | 12/2007 |
| EP | 0465241 A2 | 1/1992 |
| EP | 0465241 B1 | 11/1998 |
| EP | 1179319 A1 | 2/2002 |
| EP | 1503664 A2 | 2/2005 |
| EP | 2030565 A1 | 3/2009 |
| EP | 2534597 A2 | 12/2012 |
| EP | 3048954 A1 | 8/2016 |
| EP | 3048962 A1 | 8/2016 |
| EP | 3048963 A2 | 8/2016 |
| EP | 3048964 A1 | 8/2016 |
| EP | 3144851 A1 | 3/2017 |
| EP | 3193703 A1 | 7/2017 |
| EP | 3193704 A1 | 7/2017 |
| EP | 3193705 A1 | 7/2017 |
| EP | 3240475 A1 | 11/2017 |
| EP | 3267881 A1 | 1/2018 |
| EP | 3267887 A1 | 1/2018 |
| EP | 3307151 A1 | 4/2018 |
| EP | 2534597 B1 | 10/2018 |

(56) References Cited

FOREIGN PATENT DOCUMENTS

| | | | |
|---|---|---|---|
| JP | 2002172096 A | 6/2002 | |
| JP | 2013524865 A | 6/2013 | |
| KR | 20150020955 A | 2/2015 | |
| WO | WO-9738626 A1 | 10/1997 | |
| WO | WO-03045224 A2 | 6/2003 | |
| WO | WO-03045224 A3 | 11/2004 | |
| WO | WO-2006048881 A2 | 5/2006 | |
| WO | WO-2011115576 A2 | 9/2011 | |
| WO | WO-2012140559 A1 | 10/2012 | |
| WO | WO-2015048191 A1 | 4/2015 | |
| WO | WO-2015048194 A1 | 4/2015 | |
| WO | WO-2016145392 A1 | 9/2016 | |
| WO | WO-2016201135 A1 | 12/2016 | |
| WO | WO-2017072250 A1 | 5/2017 | |
| WO | WO-2019038435 A1 | 2/2019 | |
| WO | WO-2019089830 A1 | 5/2019 | |

OTHER PUBLICATIONS

Almeida, et al., Multilead ECG Delineation Using Spatially Projected Leads From Wavelet Transform Loops, *IEEE Transactions On Biomedical Engineering*, 56(8):1996-2005 (Aug. 2009).

Badilini, et al., ECGScan: A Method for Conversion of Paper Electrocardiographic Printouts to Digital Electrocardiographic Files, *Journal of Electrocardiology*, 38:310-318 (Oct. 2005).

Bishop, Pattern Recognition and Machine Learning, Springer, Information Science and Statistics, 2006, ISBN-10: 0-387-31073-8, New York, NY, USA.

Boichat, et al., Wavelet-Based ECG Delineation on a Wearable Embedded Sensor Platform, Proceedings of Wearable and Implantable Body Sensor Networks,*2009 Sixth International Workshop on Wearable and Implantable Body Sensor Networks*, IEEE (pp. 256-261) (Jun. 2009).

Chazal, et al., A Patient-Adapting Heartbeat Classifier Using ECG Morphology and Heartbeat Interval Features, IEEE Transactions on Biomedical Engineering, 53(12):2535-2543 (Dec. 2006).

Chazal, et al., Automatic Classification of Heartbeats Using ECG Morphology and Heartbeat Interval Features, *IEEE Transactions on Biomedical Engineering*, 51 (7):1196-1206 (Jul. 2004).

Chebil, et al., A Novel Method for Digitizing Standard ECG Papers, *Proceedings of the International Conference on Computer and Communication Engineering 2008*, May 13-15, 2008, Kuala Lumpur, Malaysia (pp. 1308-1312).

Choi, et al., Development of ECG Beat Segmentation Method by Combining Lowpass Filter and Irregular R-R Interval Checkup Strategy, Expert Systems with Applications, 37:5208-5218 (Jul. 2010).

Coast, et al., An Approach to Cardiac Arrhythmia Analysis Using Hidden Markov Models, *IEEE transactions on biomedical engineering*, 37(9):826-836 (Sep. 1990).

Cybenko, Approximation by Superpositions of a Sigmoidal Function, *Mathematics of Control, Signals and Systems*, 2(4):303-314 (Dec. 1989).

Donahue et al., Long-term Recurrent Convolutional Networks for Visual Recognition and Description, *arXiv:1411.4389v3*, (pp. 1-13) (Feb. 2015).

Dubois, et al., Automatic ECG Wave Extraction in Long-Term Recordings using Gaussian Mesa Function Models and Nonlinear Probability Estimators, *Computer Methods and Programs in Biomedicine*, 88:217-233 (Mar. 2007).

European Search Report & Written Opinion dated Oct. 15, 2018 in EP Patent Appl. Serial No. 18305376.8 (0530).

European Search Report dated Apr. 13, 2016 in EP Patent Appl. Serial No. 15191769.7 (0230).

Fukushima., Neocognitron: A Self-organizing Neural Network Model for a Mechanism of Pattern Recognition Unaffected by Shift in Position, *Biological Cybernetics*, 36:193-202 (1980).

Hughes, et al., Markov Models for Automated ECG Interval Analysis, Proceedings of Neural Information Processing Systems, 2004, Oxford, UK, (pp. 611-618).

Ieva, et al., Multivariate Functional Clustering for the Morphological Analysis of Electrocardiograph Curves, Journal of the Royal Statistical Society: Series C (Applied Statistics), 62(3):401-418 (May 2013).

International Search Report & Written Opinion dated Aug. 1, 2019 in Int'l PCT Patent Appl. No. PCT/IB2019/052517 (0510).

International Search Report & Written Opinion dated Nov. 21, 2018 in Int'l PCT Patent Appl. Serial No. PCT/EP2018/072912 (0410).

International Search Report & Written Opinion dated Jun. 4, 2020 in PCT Patent Appl. Serial No. PCT/IB2020/050850 (0710 PCT).

International Search Report & Written Opinion dated Jan. 24, 2017 in Int'l PCT Patent Appl. Serial No. PCT/EP2016/075972 (0310).

Jin, et al., Deep Learning Research on Clinical Electrocardiogram Analysis, *Science China Press*, 45(3):398-416 (2015), English abstract provided.

Johnson, et al., R-Peak Estimation using Multimodal Lead Switching, *Computing in Cardiology 2014*, IEEE, pp. 281-284 (Sep. 2014).

Kaur et al., Comparison of Different Approaches for Removal of Baseline Wander From ECG Signal, *Proceedings of the International Conference & Workshop on Emerging Trends in Technology*, (pp. 30-36) (Feb. 2011).

Kiranyaz, et al., Convolutional Neural Networks for Patient-Specific ECG Classification, *2015 37th Annual International Conference of the IEEE Engineering in Medicine and Biology Society (EMBC)*, IEEE (pp. 2608-2611) (Aug. 2015).

Kiranyaz, et al., Real-Time Patient-Specific ECG Classification by 1-D Convolutional Neural Networks, *IEEE transactions on Biomedical Engineering*, 63(3):664-675 (Aug. 2015).

Krizhevsky, et al., ImageNet Classification with Deep Convolutional Neural Networks, *Advances in neural information processing systems*, 25:1097-1105 (2012).

Laguna, et al., A Database for Evaluation of Algorithms for Measurement of QT and Other Waveform Intervals in the ECG, *Computers in Cardiology 1997*, 24:673-676.

Lecun, et al., Backpropagation Applied to Handwritten Zip Code Recognition, *Neural Computation*, 1(4):541-551 (Dec. 1989).

Li, et al., Deep neural networks Improve Atrial Fibrillation Detection in Holter: first results, *European Journal of Preventive Cardiology*, Abstract, 23 (2S) (Oct. 2016).

Li, et al., Detection of ECG Characteristic Points Using Wavelet Transforms, *IEEE Transactions on Biomedical Engineering*, 42(1):21-28 (Jan. 1995).

Lin et al., Beat-to-beat P and T Wave Delineation in ECG Signals using a Marginalized Particle Filter, *2012 Proceedings of the 20th European Signal Processing Conference (EUSIPCO)*, (pp. 479-483) (Aug. 2012).

Lin, et al., P and Twave Delineation and Waveform Estimation in ECG Signals Using a Block Gibbs Sampler, *2011 IEEE International Conference on Acoustics, Speech and Signal Processing (ICASSP)*, (pp. 479-483) (May 2011).

Lin et al., P- and T-Wave Delineation in ECG Signals Using a Bayesian Approach and a Partially Collapsed Gibbs Sampler, *IEEE Transactions on Biomedical Engineering*, 57(12):2840-2849 (Sep. 2010).

Long, et al., Fully Convolutional Networks for Semantic Segmentation, *Proceedings of The IEEE Conference On Computer Vision and Pattern Recognition*, (pp. 3431-3440) (2015).

Martinez et al., A Wavelet-Based ECG Delineator: Evaluation on Standard Databases, *IEEE Transactions on Biomedical Engineering*, 51 (4): 570-581 (Mar. 2004).

Matan, et al., Multi-Digit Recognition Using a Space Displacement Neural Network, *Neural Information Processing Systems*, 2:488-495) (Jan. 1991).

Meghriche, et al., On the Analysis of a Compound Neural Network for Detecting Atrio Ventricular Heart Block (AVB) in an ECG Signal, *International Journal of Biological and Medical Sciences*, 1(1):1-11 (Mar. 2008).

Megriche, et al., On the Analysis of a Compound Neural Network for Detecting Atrio Ventricular Heart Block (AVB) in a ECG Signal, *International Journal of Medical, Health, Biomedical, Bioengineering and Pharmaceutical Engineering*, 2(3):68-78 (2008).

Mnih, et al., Recurrent Models of Visual Attention, *arXiv:1406.6247v1:1406.6247* (Jun. 2014).

(56) References Cited

OTHER PUBLICATIONS

"Neural Nets and Noise Filtering", Dr. Dobb's Journal, pp. 32 (Jan. 1989).
Noda, et al., Audio-Visual Speech Recognition using Deep Learning, *Applied Intelligence*, 42(4):722-737, (Jun. 2015).
Nowlan, et al., A Convolutional Neural Network Hand Tracker, *Advances in Neural Information Processing Systems 7*, (pp. 901-908) (Jan. 1995).
Pan, et al., A Real-Time QRS Detection Algorithm, *IEEE Transactions on Biomedical Engineering*, 3:230-236 (Mar. 1985).
Pigoli, et al., Wavelets in Functional Data Analysis: Estimation of Multidimensional Curves and their Derivatives, *Computational Statistics & Data Analysis*, 56(6):1482-1498 (Jun. 2012).
Portet, F., P Wave Detector with PP Rhythm Tracking: Evaluation in Different Arrhythmia Contexts, *Physiological Measurement*, 29(1):141-155 (Jan. 2008).
Prineas et al., The Minnesota Code Manual of Electrocardiographic Findings, Springer, Second Edition, ISBN 978-1-84882-777-6, 2009, Minneapolis, Minnesota, US.
Ravichandran, et al., Novel Tool for Complete Digitization of Paper Electrocardiography Data, *IEEE Journal of Translational Engineering in Health and Medicine, Medical Imaging and Diagnostic Radiology*, 1:1800107 (Jun. 2013).
Rodrigues, et al., A Neural Network Approach to ECG Denoising, *arXIV preprint arXiv:1212-5217* (Dec. 2012).
Rosenblatt, The Perceptron: A Probabilistic Model for Information Storage and Organization in the Brain, *Psychological Review*, 65(6):386-408 (Nov. 1958).
Russakovsky, et al., "ImageNet Large Scale Visual Recognition Challenge", *International Journal of Computer Vision*, 115(3):211-252 (Dec. 2015).
Saini, et al., Automated ECG Delineation using Machine Learning Algorithms, *International Congress on Electrocardiology*, Jalandhar, India, 2014, (pp. 1-4).
Schluter, et al., Improved Musical Onset Detection With Convolutional Neural Networks, *IEEE International Conference on Acoustics, Speech, and Signal Processing (ICASSP )*, (pp. 6979-6983) (May 2014).
Shen, et al., Multi-Lead ECG Classification Based on Independent Component Analysis and Support Vector Machine, *3rd International Conference on Biomedical Engineering and Informatics (BMEI)*, 3:960-964 (Oct. 2010).
Simonyan, et al., Very Deep Convolutional Networks for Large-Scale Image Recognition, *arXiv preprint arXiv:1409.1556* (Sep. 2014).
Smith, et al., Improved Interpretation of Atrial Dysrhythmias by a New Neural Network Electrocardiogram Interpretation Algorithm, *Society for Academic Emergency Medicine Abstracts*, 24 (S1), S235 (2017).
Statement of Validation and Accuracy for the Glasgow 12-Lead ECG Analysis Program, Physio Control, Mar. 2009, Redmond, WA USA.
Tun, et al., Analysis on conversion process from paper record ECG to computer based ECG, *MOJ Applied Bionics and Biomechanics*, 1(2):69-81 (2017).
VAESSEN., An approach to ECG Delineation using Wavelet Analysis and Hidden Markov Models, Universiteit Maastricht Institute of Instrument Development Engineering & Evaluation Master Thesis, (Sep. 2006).
Zeiler, Matthew D., Adadelta: An Adaptive Learning Rate Method, *arXiv preprint arXiv:1212.5701*(Dec. 2012).
Zhang et al., Improving Object Detection with Deep Convolutional Networks via Bayesian Optimization and Structured Prediction, *Proceedings of the IEEE Conference on Computer Vision and Pattern Recognition*, (pp. 249-258) (2015).
Zheng, et al., Time Series Classification Using Multi-Channels Deep Convolutional Neural Networks, *International Conference on Web-Age Information Management*, (pp. 298-310), (Jun. 2014).
Extended EP Search Report dated Apr. 21, 2021 in EP Patent Application Serial No. 20211449.2 (0431).

\* cited by examiner

165

166

167

173

168

ELECTROCARDIOGRAM PROCESSING SYSTEM FOR DELINEATION AND CLASSIFICATION

CROSS-REFERENCE TO RELATED APPLICATIONS

This application is a continuation of U.S. patent application Ser. No. 16/267,380, filed on Feb. 4, 2019, now U.S. Pat. No. 10,959,660, which is a continuation-in-part of U.S. patent application Ser. No. 15/771,807, filed on Apr. 27, 2018, now U.S. Pat. No. 10,779,744, which is a national stage of PCT/EP2016/075972, filed Oct. 27, 2016, which is a continuation-in-part of U.S. patent application Ser. No. 14/924,239, filed on Oct. 27, 2015, now U.S. Pat. No. 10,426,364, and claims priority to European Application Ser. No. 15191769.7, filed on Oct. 27, 2015, the entire contents of each of which are incorporated herein by reference. U.S. patent application Ser. No. 16/267,380 is also a continuation-in-part of PCT/EP2018/072912, filed on Aug. 24, 2018, which claims priority to U.S. Provisional Application No. 62/549,994, filed on Aug. 25, 2017, the entire contents of each of which are incorporated herein by reference.

TECHNICAL FIELD

The present disclosure relates, in general, to an electrocardiogram (ECG) processing system, for example, an ECG system with artificial intelligence and having delineation and classification machine learning functionality and facilitating visualization of a large volume of ECG related data.

BACKGROUND

An electrocardiogram (ECG) receives electrical cardiac signals from the heart that may be digitized and recorded by a computing device. An ECG typically is generated from cardiac signals sensed by a number of electrodes placed in specific areas on a patient. It is a simple, non-invasive tool, that may be used by most any healthcare professional.

A cardiac signal is composed of one or multiple synchronized temporal signals. FIG. 1A illustrates a recording of a standard 12-lead resting ECG. As is shown in FIG. 1A, each lead generates an electrical signal, resulting in 12 electrical signals. Though the ECG illustrated in FIG. 1A involves 12 leads resulting in 12 recordings, some ECGs may involve fewer leads resulting in fewer recordings. As is shown in FIG. 1A, a cardiac signal displays repeating patterns usually comprising a P-wave, a QRS complex, and a T-wave. As the name suggests, a QRS complex includes a Q-wave, an R-wave and an S-wave. An exemplary P-wave, QRS complex, and T-wave is illustrated in FIG. 1B, which focuses on a couple of beats in one lead signal, showing one R-R interval.

To make a diagnosis, a trained healthcare professional may analyze the ECG recording to identify any abnormalities and/or episodes. It is estimated that about 150 measurable abnormalities may be identified on an ECG recordings today. However, specific expertise and/or training is required to identify abnormalities from an ECG. ECG analysis is only available to those patients that can afford healthcare professions having the appropriate expertise and who otherwise have access to these professionals.

Telecardiology centers have been developed to provide ECG analysis to patients that may not otherwise have access to these trained healthcare professionals. Typically, an ECG recording is generated offsite by a non-specialist and is sent to the telecardiology center for analysis by a cardiologist or by a specialized ECG technician. While the results are generally high quality, the process may be slow and expensive.

Software systems have also been developed as an alternative to analysis by a trained professional. Current software systems provide a low quality interpretation that often results in false positives. Today, these interpretation systems may generate two types of information about a cardiac signal, (1) temporal location information for each wave, referred to as delineation, and (2) global information providing a classification of the cardiac signal or labeling its abnormalities, referred to as classification.

Concerning delineation, two main approaches are used for finding the waves of cardiac signals. The first approach is based on multiscale wavelet analysis. This approach looks for wavelet coefficients reaching predefined thresholds at specified scales. (See Martinez et al., A wavelet-based ECG delineator: evaluation on standard databases, IEEE transactions on biomedical engineering, Vol. 51, No. 4., April 2004, pp. 570-58; Almeida et al., IEEE transactions on biomedical engineering, Vol. 56, No. 8, August 2009, pp 1996-2005; Boichat et al., Proceedings of Wearable and Implantable Body Sensor Networks, 2009, pp. 256-261; U.S. Pat. No. 8,903,479 to Zoicas et al.). The usual process involves identifying QRS complexes, then P-waves, and finally T-waves. This approach is made unstable by the use of thresholds and fails to identify multiple P-waves and "hidden" P-waves.

The second delineation approach is based on Hidden Markov Models (HMM). This machine learning approach treats the current state of the signal as a hidden variable that one wants to recover (Coast et al., IEEE transactions on biomedical engineering, Vol. 37, No. 9, September 1990, pp 826-836; Hughes et al., Proceedings of Neural Information Processing Systems, 2004, pp 611-618; U.S. Pat. No. 8,332, 017 to Trassenko et al.). While this approach is an improvement upon on the first delineation approach described above, a representation of the signal must be designed using handcrafted "features," and a mathematical model must be fitted for each wave, based on these features. Based on a sufficient number of examples, the algorithms may learn to recognize each wave. This process may however be cumbersome and inaccurate due to its dependence on handcrafted features. Specifically, features which have been handcrafted will always be suboptimal since they were not learnt and the process of handcrafting features may have ignored or eliminated crucial information. Further, the model, usually Gaussian, is not well adapted. Also, the current models fail to account for hidden P waves.

Regarding classification, in current systems analysis is only performed on the QRS complex. For example, analysis of a QRS complex may detect ventricular or paced beats. The training involves handcrafted sets of features and corresponding beat labels (Chazal et al., IEEE Transactions on Biomedical Engineering, 2004, vol. 51, pp. 1196-1206). As explained above, features that have been handcrafted will always be suboptimal since they were not learnt and the process of handcrafting features may have ignored or eliminated crucial information.

To solve the above issues, recent works (Kiranyaz et al., IEEE Transactions on Biomedical Engineering, 2016, Vol. 63, pp 664-675) have turned to novel architectures called neural networks which have been intensively studied and had great results in the field of imaging (Russakovsky et al., arXiv: 1409.0575v3, 30 Jan. 2015). Neural networks learn from raw or mildly preprocessed data and thus bypass the need of handcrafted features. While the application of neural networks is an improvement on the delineation and classification approaches described above, current systems have certain drawbacks. For example, the current neural networks were only developed for QRS characterization. Further, current neural networks processes information in a beat-by-beat manner which fails to capture contextual information from surrounding beats.

Concerning identifying abnormalities and/or cardiovascular disease detection, most algorithms use rules based on temporal and morphological indicators computed using the delineation (e.g., PR interval, RR interval, QT interval, QRS width, level of the ST segment, slope of the T-wave). Often times, the algorithms are designed by cardiologists. (Prineas et al., The Minnesota Code Manual of Electrocardiographic Findings, Springer, ISBN 978-1-84882-777-6, 2009). However, the current algorithms do not reflect the way the cardiologists analyze the ECGs and are crude simplifications. For example, the Glasgow University Algorithm does not reflect the way cardiologist analyze ECGs. (Statement of Validation and Accuracy for the Glasgow 12-Lead ECG Analysis Program, Physio Control, 2009.)

More advanced methods have also been developed that use learning algorithms. In. Shen et al., Biomedical Engineering and Informatics (BMEI), 2010. vol. 3, pp. 960-964, for instance, the author used support vector machines to detect bundle branch blocks. However, in these methods, once again, it is necessary to represent the raw data in a manner that preserves the invariance and stability properties.

While more complex neural network architectures have been proposed, limitations arose when they were applied to ECGs. One team (Jin and Dong, Science China Press, Vol. 45, No 3, 2015, pp 398-416; CN104970789) proposed binary classification on a full ECG, hence providing one and only one classification for any analyzed ECG. The proposed architecture used convolutional layers which processes the leads independently before mixing them into fully connected layers. The authors also mention multi-class analysis, as opposed to binary analysis, aiming at recovering one class among several. However, they did not consider multi-label classification, wherein multiple labels (e.g., abnormalities) are assigned to a cardiac signal.

In view of the foregoing limitations of previously-known systems and methods, it would be desirable to accurately and efficiently process ECG data and to present this information in a way that is easily comprehendible. For example, it may be desirable to obtain delineation and classification of an ECG signal in a manner that does not require feature extraction, to identify hidden P-waves, to analyze an ECG signal over multiple beats, and to achieve multi-label classifications for a cardiac signal.

SUMMARY OF THE INVENTION

Provided herein are systems and methods for analyzing ECG data using machine learning algorithms and medical grade artificial intelligence with enhanced accuracy and efficiency. Specifically, systems and methods are provided for analyzing electrocardiogram (ECG) data of a patient using artificial intelligence and a substantial amount of ECG data. The systems receive ECG data from a sensing device positioned on a patient such as one or more ECG leads. The system may include an application that communicates with an ECG platform running on a server that processes and analyzes the ECG data, e.g., using neural networks for delineation of the cardiac signal and classification of various abnormalities, conditions and/or descriptors. The ECG platform may be a cloud-based ECG platform that processes and analyzes the ECG data in the cloud. The processed ECG data is communicated from the server for display in a user-friendly and interactive manner with enhanced accuracy. Together the ECG application and ECG platform implement the ECG processing system to receive ECG data, process and analyze ECG data, display ECG data on a system device, and generate a report having ECG data.

A system for analyzing ECG data of a patient may, in one example, involve a first plurality of instructions designed to, when executed, obtain ECG data of the patient over a plurality of time points and may further cause transmission of the ECG data to at least one server. The ECG data may be sampled at a predetermined sampling rate such as a rate of at least 20 samples per second. The system for analyzing ECG data may further involve a second plurality of instructions designed to, when executed, cause the at least one server to receive the ECG data of the patient, analyze the ECG data of the patient using at least one algorithm trained from a plurality of ECG data sets from different patients, quantify a likelihood of a presence of one or more abnormalities, conditions, or descriptors, or any combination thereof, and transmit information corresponding to the presence of the one or more abnormalities, conditions, or descriptors, or any combination thereof, to a computer remote from the at least one server for display.

The system for analyzing ECG data may further involve a third plurality of instructions designed to, when executed by the computer, cause the computer to display information corresponding the presence of the one or more abnormalities, conditions, or descriptors, or any combination thereof, based on the transmitted information from the at least one server. It is understood that each set of the plurality of ECG data sets from the different patients may be generated at a sampling rate equal to the rate used to obtain the ECG data. It is further understood that the computer that executes the third plurality of instructions may also execute the first plurality of instructions.

The second plurality of instructions may, when executed, further cause the at least one server to pre-process the ECG data which may involve removing noise from the ECG data or expressing the ECG data at a predetermined baseline frequency. Further, the second plurality of instructions, when executed, may analyze the ECG data of the patient using at least one algorithm that applies the ECG data to a first neural network for delineation and may further quantify a likelihood of a presence of at least one of a P-wave, QRS complex, or T-wave at each of the plurality of time points. The second plurality of instructions may further calculate at least one onset and at least one offset for at least one of the P-wave, QRS-complex, or T-wave, and/or calculate at least one measurement from one or more of the onset, the offset, or the output of the first neural network.

It is further understood that the second plurality of instructions may, when executed, analyze the ECG data of the patient using at least one algorithm that applies the ECG data to a second neural network for classification. Specifically, the second plurality of instructions may quantify a likelihood of a presence of the one or more abnormalities, conditions, or descriptors, and may apply a threshold to at least one value in the output of the second neural network and assign at least one label corresponding to the one or more abnormalities, conditions, or descriptors if the value exceeds a threshold. The second plurality of instructions may also post-process the ECG data by removing redundant labels.

The system may further include a fourth and/or fifth plurality of instructions. The fourth plurality of instructions may, when executed, cause the at least one server to generate a report including at least the transmitted information corresponding to the presence of the one or more abnormalities, conditions, or descriptors. The fifth plurality of instructions may, when executed, receive user input related to the ECG data and cause the computer to transmit the user input to the at least one server such that the at least one server uses the user input to generate the report. The report may include at least one heart rate density plot representing density of heart rates of the patient as a function of time. It is understood that a third plurality of instructions is further configured to, when executed by the computer, cause the computer to display a heart rate density plot representing density of heart rates of the patient as a function of time.

A system for analyzing ECG data of a patient may, in another example, involve instructions stored on at least one server that are designed to, when executed, cause the at least one server to receive a set of ECG data of the patient over a plurality of time points. The set of ECG data may be sampled at a predetermined sampling rate such as a rate of at least 20 samples per second. The instructions may further be designed to cause the at least one server to analyze the set of ECG data of the patient using at least one algorithm, quantify, at each time point of the plurality of time points, a likelihood of a presence of one or more abnormalities, conditions, or descriptors, or any combination thereof and transmit information corresponding to the likelihood of the presence of the one or more abnormalities, conditions, or descriptors to a computer for display. The at least one algorithm may be trained using a plurality of sets of ECG data generated at a sampling rate of at least 20 samples per second from different patients.

A computerized-method for analyzing ECG data of a patient may similarly involve receiving a set of ECG data of the patient over a plurality of time points sampled at a sample rate and analyzing the set of ECG data of the patient using at least one algorithm trained using a plurality of sets of ECG data. Each set in the plurality of sets of ECG data may be generated at the same sample rate from different patients. The computerized method for analyzing ECG data may further involve identifying, at each time point, one or more abnormalities, conditions or descriptors, or any combination thereof and further may involve transmitting information comprising the one or more abnormalities, conditions, or descriptors, or any combination thereof to a computer for display. It is understood that the computerized-method may involve analyzing an entire set of sampled ECG data without discarding data from the set of ECG data. The computerized-method may, in one example, involve a sample rate of at least 20 samples per second.

The foregoing summary is illustrative only and is not intended to be in any way limiting. In addition to the illustrative aspects, embodiments, and features described above, further aspects, embodiments, and features will become apparent by reference to the following drawings and the detailed description.

The foregoing and other features of the present invention will become apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings.

DETAILED DESCRIPTION OF THE INVENTION

The present invention is directed to an electrocardiogram (ECG) processing system having medical grade artificial intelligence involving an ECG application run on a system device and an ECG platform run on a server(s). The ECG application and ECG platform implement the ECG processing system by processing and analyzing the ECG data using machine learning algorithms to achieve delineation of the cardiac signal and classification of various abnormalities, conditions, and descriptors. The server(s) may be located in a different location than the system device(s) and the servers need not be in the same physical location as one another (e.g., the server(s) may be a remote server(s)). Alternatively, the server(s) and the system device(s) may be located in the same general area (e.g., on a local area network (LAN)). The ECG platform may be a cloud-based ECG platform that may implement the ECG processing system by processing and analyzing the ECG data in the cloud.

To implement the ECG processing system, ECG application running on the system device may receive ECG data (i.e., cardiac signal) from a sensing device and may transmit the ECG data to a ECG platform running on the server. The ECG platform may execute a first and second neural network and may apply the ECG data to the first and second neural network. The first neural network may be a delineation neural network having machine learning functionality. The second neural network may be a classification neural network having machine learning functionality. The output of the first and/or second neural networks may be processed by the ECG platform to achieve delineation and classification of the ECG data. The ECG data and/or data generated by the ECG platform may be communicated from the ECG platform to the ECG application. The ECG application may cause the ECG data and/or data generated by the ECG platform to be displayed in an interactive manner. The ECG platform may generate reports including ECG data and/or data generated by the ECG platform, and may communicate the reports to the ECG application.

Figure 1A:
FIG. 1A is a recording of a standard 12-lead resting ECG and FIG. 1B is a recording of an exemplary P-wave, QRS complex and T-wave.
Figure 1B:
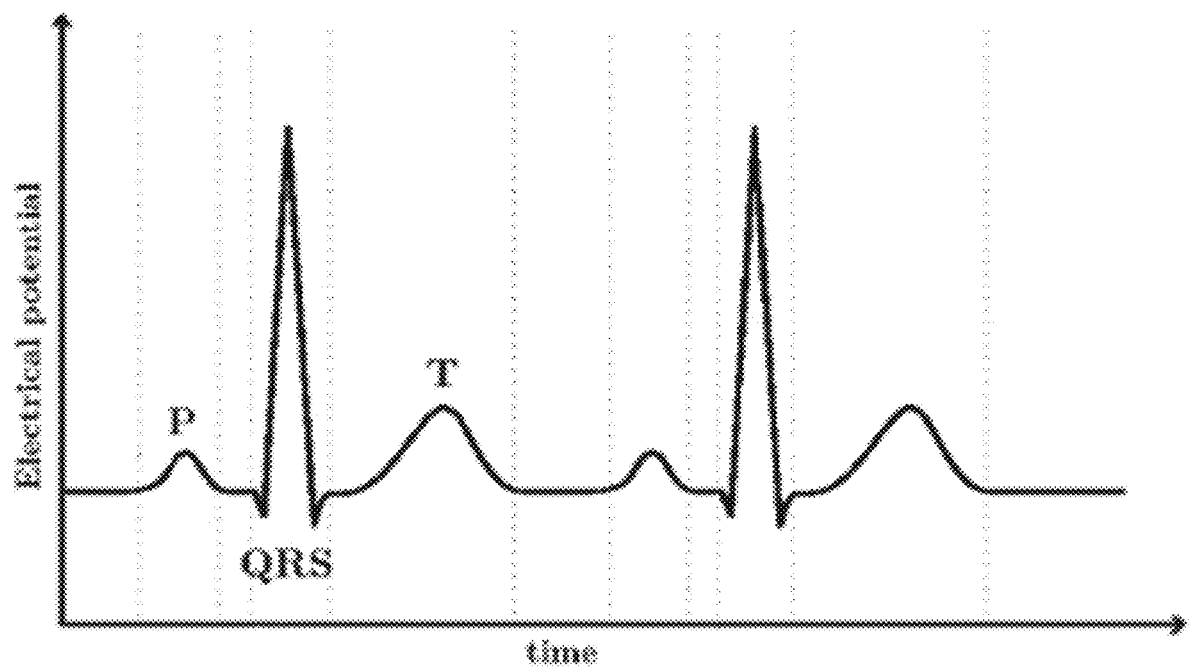
Figure 2:
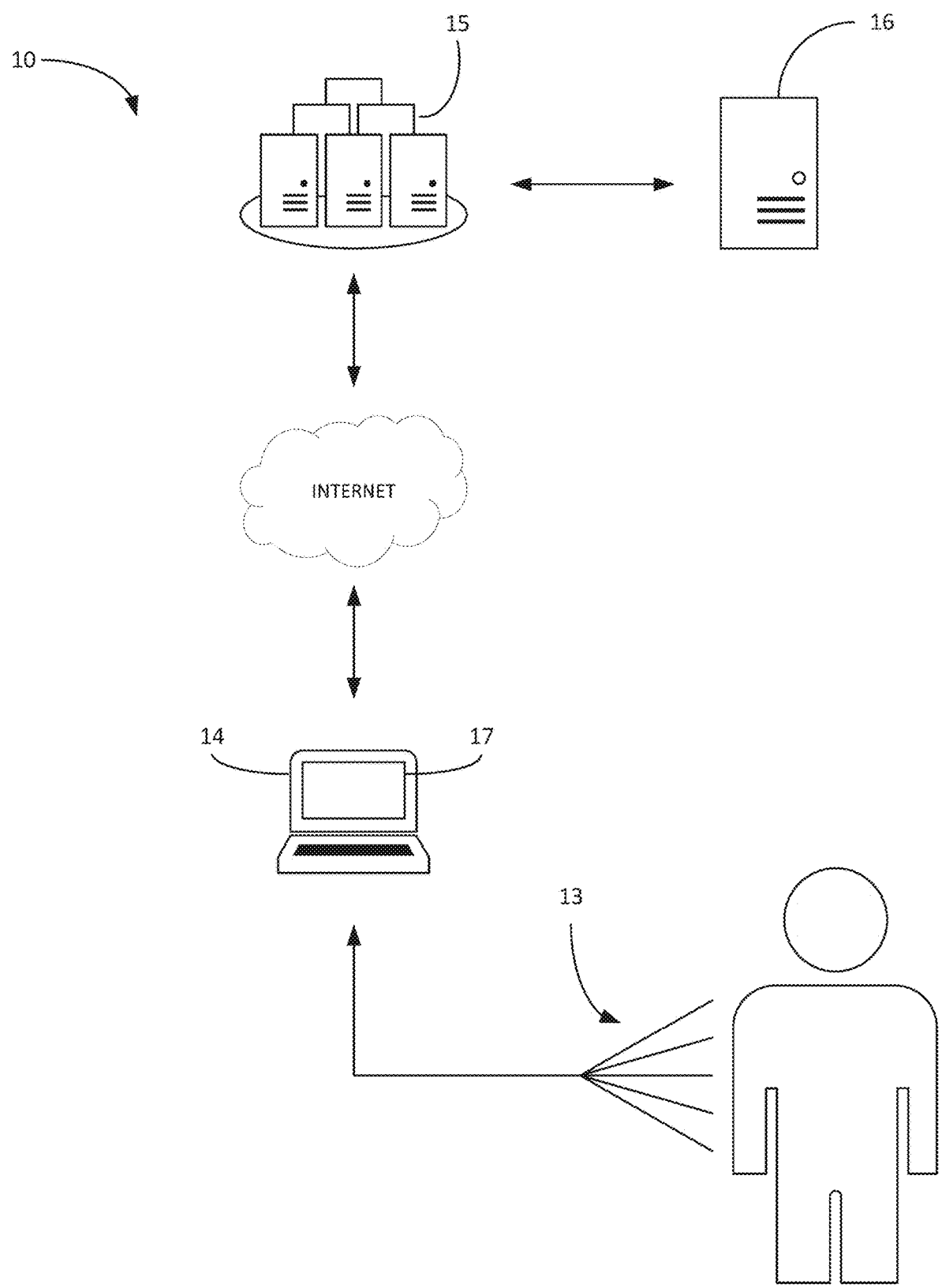
FIG. 2 is a diagram illustrating exemplary components for executing systems and methods in accordance with aspect of the present disclosure.

Referring now to FIG. 2, exemplary components for executing electrocardiogram (ECG) processing system 10 are illustrated. FIG. 2 shows ECG sensing device 13, system device 14, and server 15, as well as drive 16.

ECG sensing device 13 is designed to sense the electrical activity of the heart for generating ECG data. For example, sensing device 13 may be one or more electrodes that may be disposed on one or more leads. ECG sensing device 13 may be an ECG-dedicated sensing device such as a conventional 12-lead arrangement or may be a multi-purposes device with sensing hardware for sensing electrical activity of the heart for ECG generation such as the Apple Watch available from Apple, Inc., of Cupertino, Calif. Sensing device 13 may be placed on the surface of the chest of a patient and/or limbs of a patient. Sensing device 13 may be in electrical communication with system device 14 running the ECG application 29 such that the electrical signal sensed by sensing device 13 may be received by the ECG application 29. ECG application 29 may include instructions that cause sensing device 13 to sense or otherwise obtain ECG data.

System device 14 is preferably one or more computing devices (e.g., laptop, desktop, tablet, smartphone, smartwatch, etc.) having the components described below with reference to FIG. 3A and the functionality described herein. System device 14 running ECG application 29 may connect with server 15 running ECG platform 37 via any well-known wired or wireless connection. For example, system device 14 may connect to the Internet using well known technology (e.g., WiFi, cellular, cable/coaxial, and/or DSL) and may communicate with server 15 over the Internet.

Server 15 is preferably one or more servers having the components described below with reference to FIG. 3B and the functionality described herein. Server 15 preferably has processing power superior to system device 14 such that server 15 can process and analyze cardiac signals having a sampling rate above a predetermined threshold, such as at least 20 samples per second, at least 250 samples per second, or at least 1000 samples per second. As will be readily apparent to one skilled in the art, server 15 may include a plurality of servers located in a common physical location or in different physical locations. In a preferred embodiment, server 15 is located in a different, remote location (e.g., on the cloud) than system device 14, although server 15 and system device 14 may be located in a common location (e.g., on a local area network (LAN)).

Server 15 may optionally communicate with drive 16 which may be one or more drives having memory dedicated to storing digital information unique to a certain patient, professional, facility and/or device. For example, drive 16 may include, but is not limited to, volatile (e.g. random-access memory (RAM)), non-volatile (e.g. read-only memory (ROM)), flash memory, or any combination thereof. Drive 16 may be incorporated into server 15 or may be separate and distinct from server 15 and may communicate with server 15 over any well-known wireless or wired connection.

Figure 3A:
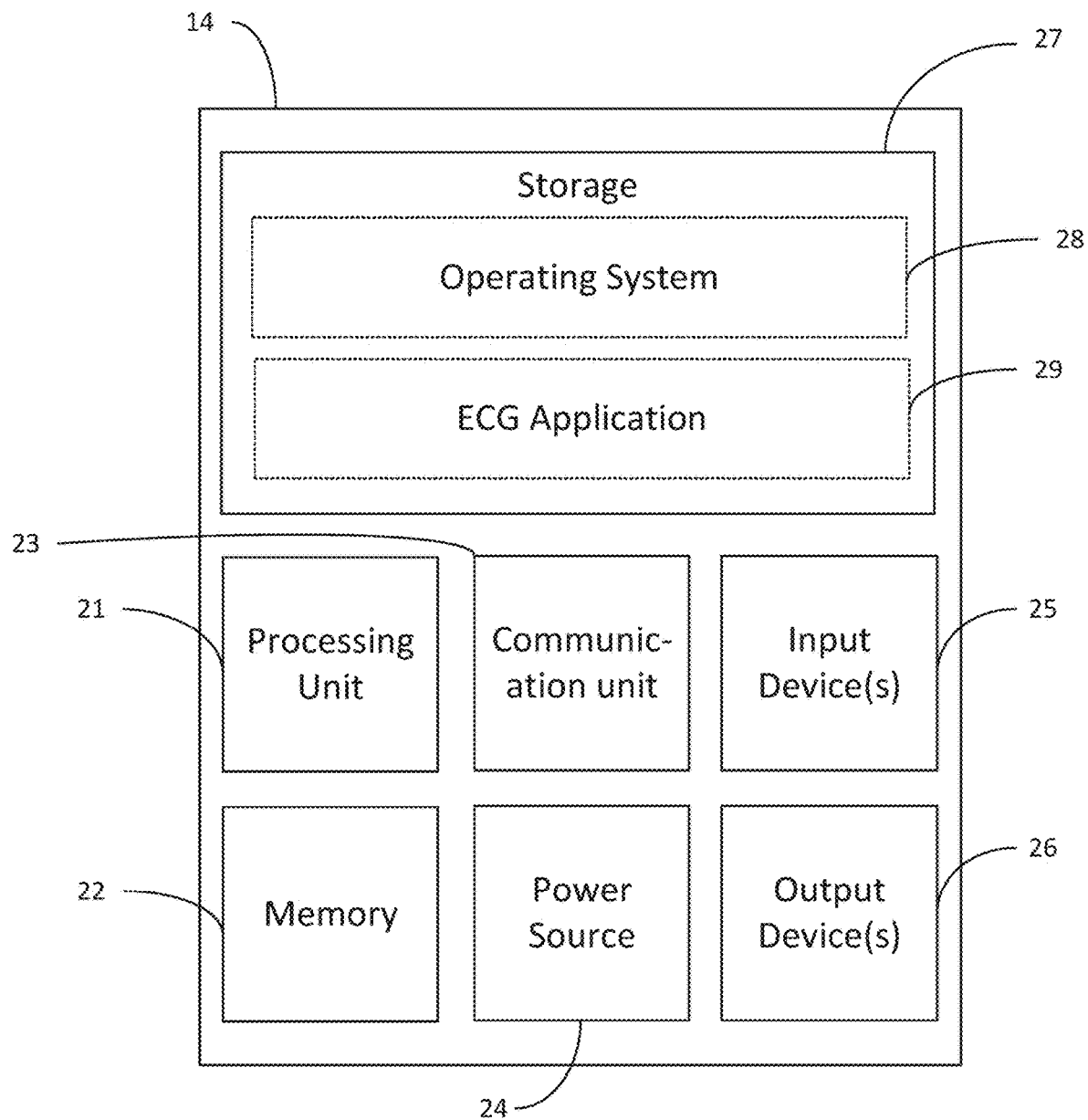
FIGS. 3A-3B are schematic views of the exemplary hardware and software components of an exemplary system device and an exemplary server, respectively.
Figure 3B:
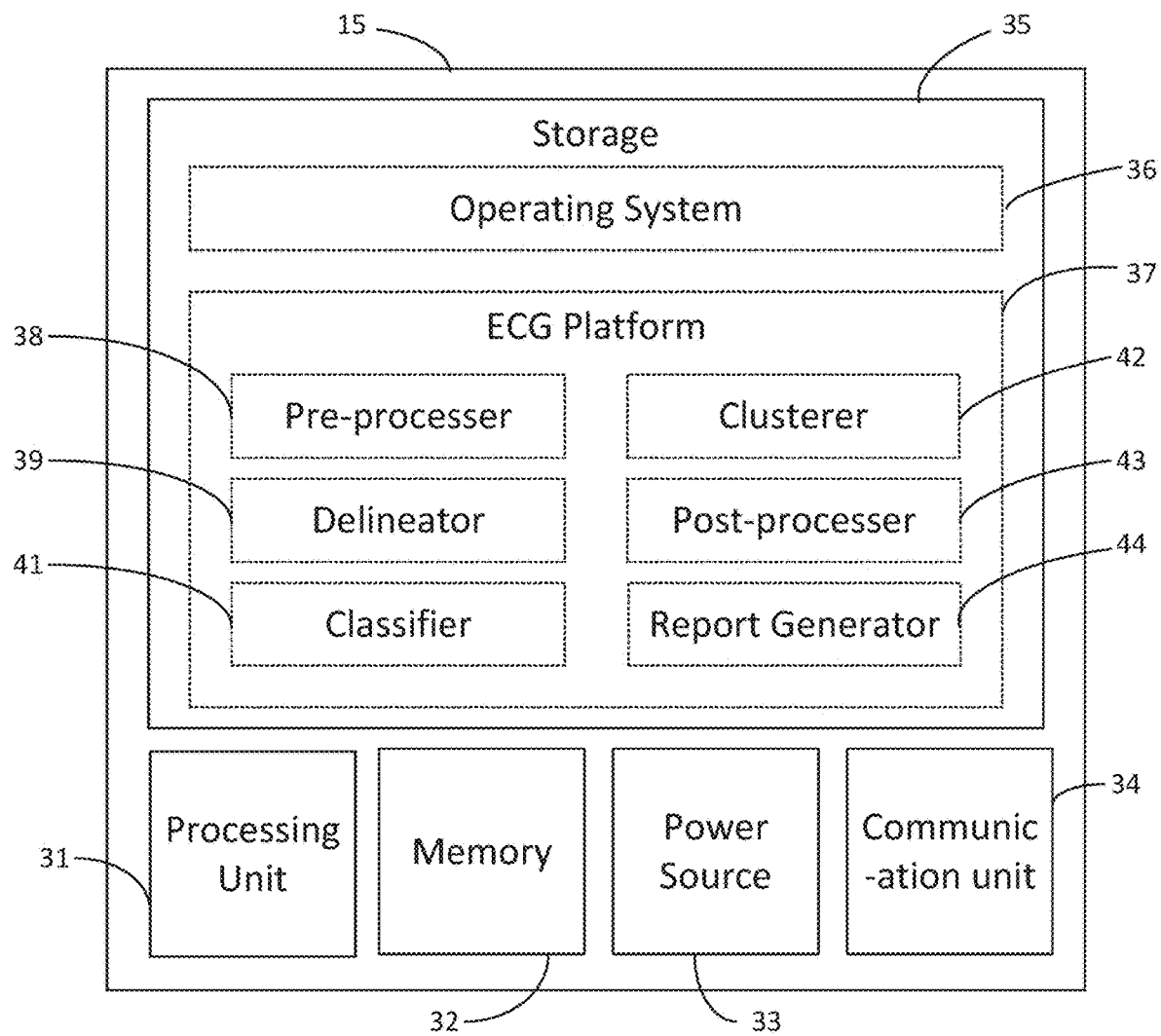

Referring now to FIGS. 3A-3B, exemplary functional blocks representing the hardware and software components of system device 14 and server 15 are shown. Referring now to FIG. 3A, hardware and software components of system device 14 may include one or more processing unit 21, memory 22, storage 27, communication unit 23, and power source 24, input devices 25 and output devices 26.

Processing unit 31 may be one or more processors configured to run collaboration operating system 28 and ECG application 29 and perform the tasks and operations of system device 14 set forth herein. Memory 22 may include, but is not limited to, volatile (e.g. random-access memory (RAM)), non-volatile (e.g. read-only memory (ROM)), flash memory, or any combination thereof. Communication unit 23 may receive and/or transmit information to and from other components in ECG processing system 10 including, but not limited to, sensing device 13 and server 15. Communication unit 23 may be any well-known communication infrastructure facilitating communication over any well-known wired or wireless connection, including over any well-known standard such as any IEEE 802 standard. Power source 24 may be a battery or may connect system device 14 to a wall outlet or any other external source of power. Storage 27 may include, but is not limited to, removable and/or non-removable storage such as, for example, magnetic disks, optical disks, or tape.

Input device 25 may be one or more devices coupled to or incorporated into system device 14 for inputting data to system device 14. Input device 25 may further include a keyboard, a mouse, a pen, a sound input device (e.g., microphone), a touch input device (e.g., touch pad or touch screen), a location sensor, and/or a camera, for example. Output device 26 may be any device coupled to or incorporated into system device 14 for outputting or otherwise displaying data and includes at least a display 17. Output device 26, may further include speakers and/or a printer, for example.

ECG application 29 may be stored in storage 27 and executed on processing unit 21. ECG application 29 may be a software application and/or software modules having one or more sets of instructions suitable for performing the operations of system device 14 set forth herein, including facilitating the exchange of information with sensing device 13 and server 15. For example, ECG application 29 may cause system device 14 to receive ECG data from sensing device 13, to record ECG data from sensing device 13, to communicate ECG data to server 15, to instruct server 15 to process and analyze ECG data, to receive processed and/or analyzed ECG data from server 15, to communicate user input regarding report generation to server, and to generate a graphic user interface suitable for displaying raw, analyzed and/or processed ECG data and data related thereto.

Operating system 28 may be stored in storage 27 and executed on processing unit 21. Operating system 28 may be suitable for controlling the general operation of system device 14 and may work in concert with ECG application 29 to achieve the functionality of system device 14 described herein. System device 14 may also optionally run a graphics library, other operating systems, and/or any other application programs. It of course is understood that system device 14 may include additional or fewer components than those illustrated in FIG. 3A and may include more than one of each type of component.

Referring now to FIG. 3B, hardware and software components of server 15 may include one or more processing unit 31, memory 32, storage 35, power source 33, and communication unit 34. Processing unit 31 may be one or more processors configured to run operating system 36 and ECG platform 37 and perform the tasks and operations of server 15 set forth herein. Given the volume of data and processing tasks assigned to processing unit 31, it is understood that processing unit 31 has superior processing power compared to processing unit 21.

Memory 32 may include, but is not limited to, volatile (e.g. random-access memory (RAM)), non-volatile (e.g. read-only memory (ROM)), flash memory, or any combination thereof. Storage 35 may include, but is not limited to, removable and/or non-removable storage such as, for example, magnetic disks, optical disks, or tape. Communication unit 34 may receive and/or transmit information to and from other components of ECG processing system 10 including, but not limited to, system device 14 and/or drive 16. Communication unit 34 may be any well-known communication infrastructure facilitating communication over any well-known wired or wireless connection. Power source 33 may be a battery or may connect server 15 to a wall outlet or other external source of power.

Operating system 36 and ECG platform 37 may be stored in storage 35 and executed on processing unit 31. Operating system 36 may be suitable for controlling general operation of server 15. ECG platform 37 may be a software application and/or software modules having one or more sets of instructions. ECG platform 37 may facilitate and oversee the processing and analysis of ECG data received from system device 14, report generation, and otherwise may be suitable for performing the operations of server 15 set forth herein.

ECG platform 37 may include several sub-modules and/or applications including, but not limited to, pre-processor 38, delineator 39, classifier 41, clusterer 42, post-processor 43 and report generator 44. Each sub-module and/or application may be a separate software application and/or module having one or more sets of instructions. Pre-processor 38 may pre-process raw ECG data, delineator 39 may execute a first neural network to achieve delineation, classifier 41 may execute a second neural network to achieve classification, clusterer 42 may identify clusters in data processed by the first neural network, post-processor 43 may post-process data processed by the second neural network, and report generator 44 may generate reports based on raw ECG data and ECG data processed by ECG platform 37. ECG platform 37 may also perform various other functions including, but not limited to, receiving requests from system device 14 to process and/or analyze ECG data, communicating processed and/or analyzed ECG data to system device 14, receiving a request to generate a report, requesting and/or receiving user interaction and/or instructions from system device 14, receiving user input data and/or instruction information from system device 14 regarding report generation, and/or communicating a report to system device 14.

Server 15 may also optionally run a graphics library, other operating systems, and/or any other application programs. It of course is understood that server 15 may include additional or fewer components than those illustrated in FIG. 3B and may include more than one of each type of component.

Figure 4:
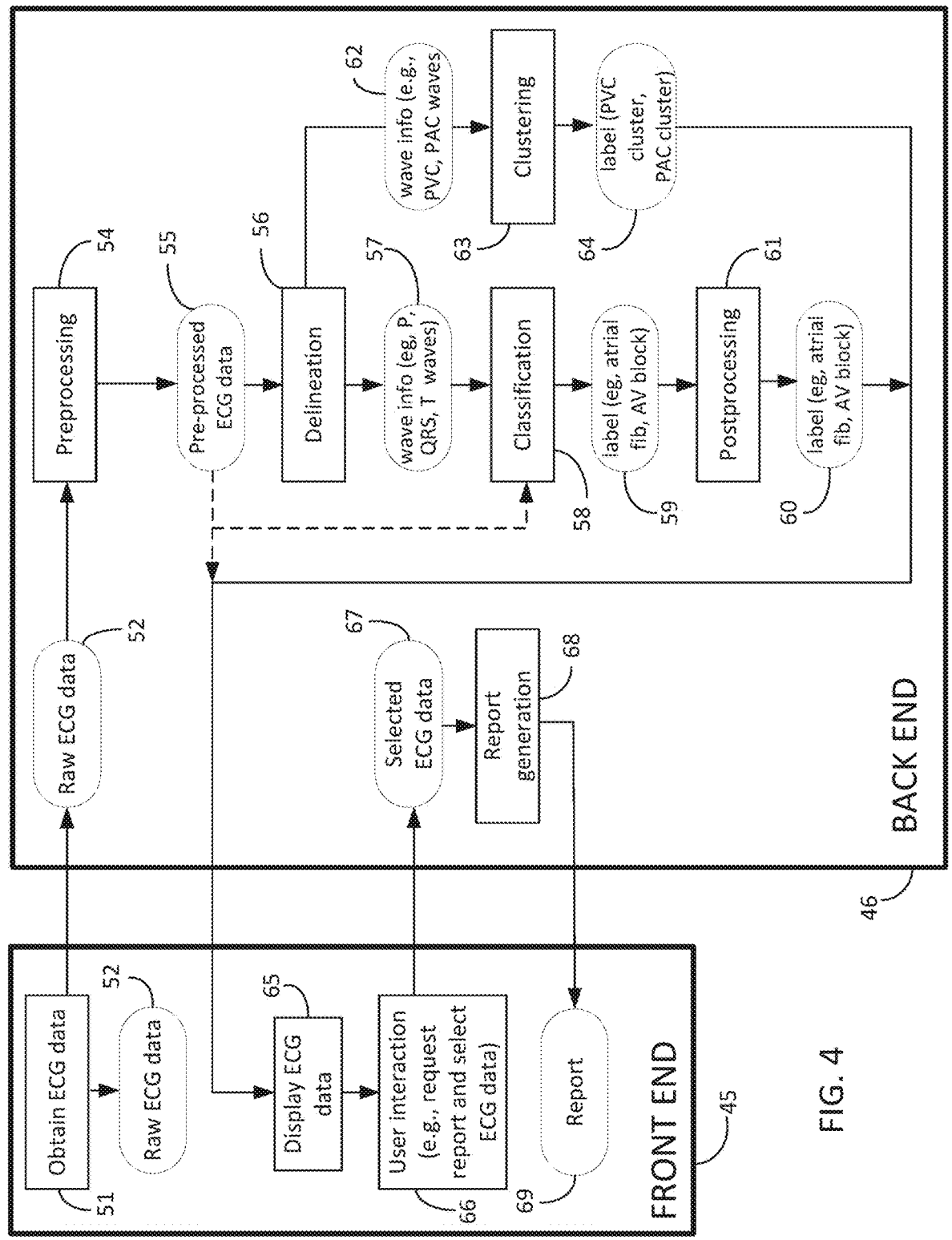
FIG. 4 is a flow chart of an exemplary method of processing ECG data using, displaying ECG data, and generating a report including ECG data.

FIG. 4 illustrates an exemplary process for implementing ECG processing system 10 to receive and record ECG data, process and analyze ECG data, and generate reports involving ECG data, and further shows the flow of information between front end 45 and back end 46 of ECG processing system 10. Front end 45 includes at least ECG application 29 running on system device 14. Back end 46 includes at least ECG platform 37 running on server 15.

As is shown in FIG. 4, at step 51, ECG application 29 may cause system device 14 to receive and/or otherwise obtain raw ECG data 52 from sensing device 13. For example, ECG application 29 may cause sensing device 13 to sense the cardiac signal and communicate the cardiac signal sensed by sensing device 13 to system device 14. Raw ECG data is the cardiac signal sensed by sensing device 13. Raw ECG data 52 has not been processed or analyzed by ECG processing system 10. Raw ECG data 52 preferably involves data sampled multiple times per heartbeat over a plurality of heartbeats. It is understood that sensing device 13 may convert an analog cardiac signal into a digital signal, a different component not shown in FIG. 2 may convert the analog cardiac signal to a digital signal, or ECG application 29 may cause system device 14 to convert the analog cardiac signal to a digital signal. Raw ECG data in both analog and digital form are referred to herein as raw ECG data 52.

Upon receiving raw ECG data 52, ECG application 29 may cause system device 14 to record raw ECG data 52 and may optionally save some or all of raw ECG data 52 to system device 14. As explained above, the signals may correspond to one or more leads. When multiple leads are used, all leads may be processed simultaneously. It is understood that the cardiac signal generated by each lead may have varying lengths. It is further understood that the cardiac signal may be short term (e.g., 10 seconds in standard ECGs) or long term (several days in holters). System device 14 may optionally display raw ECG data 52 or a portion thereof on display 17.

As is shown in FIG. 4, raw ECG data 52 may be transmitted from front end 45 to back end 46. Specifically, ECG application 29 may cause system device 14 to communicate raw ECG data 52 to ECG platform 37 running on server 15. Upon receiving raw ECG data 52, ECG platform 37 may cause server 15 to save some or all of raw ECG data 52 to server 15. Further, after receiving raw ECG data 52, ECG platform 37 cause raw ECG data 52 to be preprocessed at step 54 by pre-processor 38. It is understood that pre-processor 38 may be a stand-alone component of ECG platform 37 or subcomponent of delineator 39.

Pre-processor 38 may process raw ECG data 52 or a portion thereof by removing the disturbing elements of the cardiac signal, such as noise from the raw ECG data. For noise filtering, a multivariate functional data analysis approach may be used (Pigoli and Sangalli. Computational Statistics and Data Analysis, Vol. 56, 2012, pp 1482-1498). As the signal sensed by sensing device 13 may vary due to a patient's movements, the baseline frequency of raw ECG data 52 may be removed by pre-processor 38 and the cardiac signal may be expressed at a chosen frequency. The frequencies of the signal corresponding to the patient's movements may be removed using median filtering (Kaur et al., Proceedings published by International Journal of Computer Applications, 2011, pp 30-36). Applying raw ECG data 52 to pre-processor 38 generates pre-processed ECG data 55. At this point, ECG platform 37 may cause pre-processed ECG data 55 to optionally be communicated to ECG application 29 running on system device 14 for display on display 17. ECG platform 37 may alternatively, or additionally, cause pre-processed ECG data 55 to be used as an input at classification step 58, discussed in more detail.

At step 56, ECG platform 37 causes pre-processed ECG data 55 to be applied to delineator 39 for delineation. Delineator 39 applies a first neural network that is a delineation neural network to pre-processed ECG data 55. A neural network refers to a mathematical structure or algorithm that may take an object (e.g., matrix or vector) as input and produce another object as an output though a set of linear and non-linear operations called layers. For example, the input of the first neural network may be one or more multi-lead cardiac signals that are pre-processed to remove noise and/or baseline wandering.

To apply pre-processed ECG data 55 to the first neural network, delineator 39 may cause some or all of raw ECG data 52 to be expressed as matrix X, which may be a matrix of real numbers. For example, matrix X may be a matrix of size m×n at the frequency used for training the networks, described in more detail below. The constant "m" may be a number of leads in sensing device 13, which is typically 12, though any number of leads may be used. In this example, the number of samples "n" provides the duration of the cardiac signal "n/f" with f being the sampling frequency of the cardiac signal. The sample rate is above a predetermined rate and is preferably relatively high, such as, for example, at least 20, at least 250, at least 500 or at least 1000 samples per second, etc. In one embodiment, all of the sampled ECG data is transferred to the server for input into the processing algorithms without filtering out ECG data. While the ECG data applied to the first neural network is preferably pre-processed ECG data 55, it is understood that a non-preprocessed cardiac signal (i.e., raw ECG data 52, or a portion thereof) may be applied to the first neural network.

The first neural network may provide as an output, values corresponding to the likelihood of the presence of or one or more waves at a plurality of time points in the cardiac signal. The time points may be dictated by the raw ECG data, may be selected by the user of system device 14, or may be preprogrammed. The first neural network may be a convolutional neural network, and is preferably a fully convolutional neural network. Convolutional neural networks are a particular type of neural network where one or more matrices, which are learned, do not encode a full linear combination of the input elements, but the same local linear combination at all the elements of a structured signal, such as a cardiac signal, through a convolution (Fukushima, Biol. Cybernetics, Vol. 36, 1980, pp 193-202, LeCun et al., Neural Computation, Vol. 1, 1989, pp 541-551). A network which only contains convolutional networks is called a fully convolutional neural network.

Accordingly, at step 56, delineator 39 causes the first neural network to read each time point of the cardiac signal, spatio-temporally analyze each time point of the cardiac signal, and assign a score at each time point corresponding to one or more types of waves. In this manner, all types of waves in the cardiac signals may analyzed and the likelihood of their presence at each time point, quantified, in a single step. Accordingly, each score generated by delineator 39 is indicative of the likelihood of the presence of a particular wave type at a given time point of the cardiac signal. The wave types may be any well know wave type such as, P-waves, Q-wave, R-wave, S-wave, Q-waves, R-waves, S-waves, QRS complexes, and/or T-waves, for example. In this manner, delineator 39 may process data sampled multiple times per heart beat across a plurality of heart beats.

The output of the first neural network may be a matrix Y, which may be a matrix of real numbers. For example, matrix Y may be a matrix of the size p×n. Matrix Y may include scores for each type of wave at each time point of the cardiac signal. In matrix Y, "n" is the number of samples, as discussed above with respect to Matrix X, and "p" is the number of wave types plus the number of wave characterizations. As explained in more detail below, wave characterization may correspond to conductivity, prematurity, ectopy, and/or origin of the waves in the cardiac signal, for example. In one example, the wave types include (1) P-waves, (2) QRS complexes, and (3) T-waves, and the wave characterizations include (1) premature waves, (2) paced waves, (3) ventricular QRS complexes, (4) junctional QRS complexes, (5) ectopic P waves, and (6) non-conducted P waves. Accordingly, in this example, p=3+6=9. Each wave type may be expressed according to certain characteristics of that wave, such as start and end points (i.e., onset and offset)).

Figure 5A:
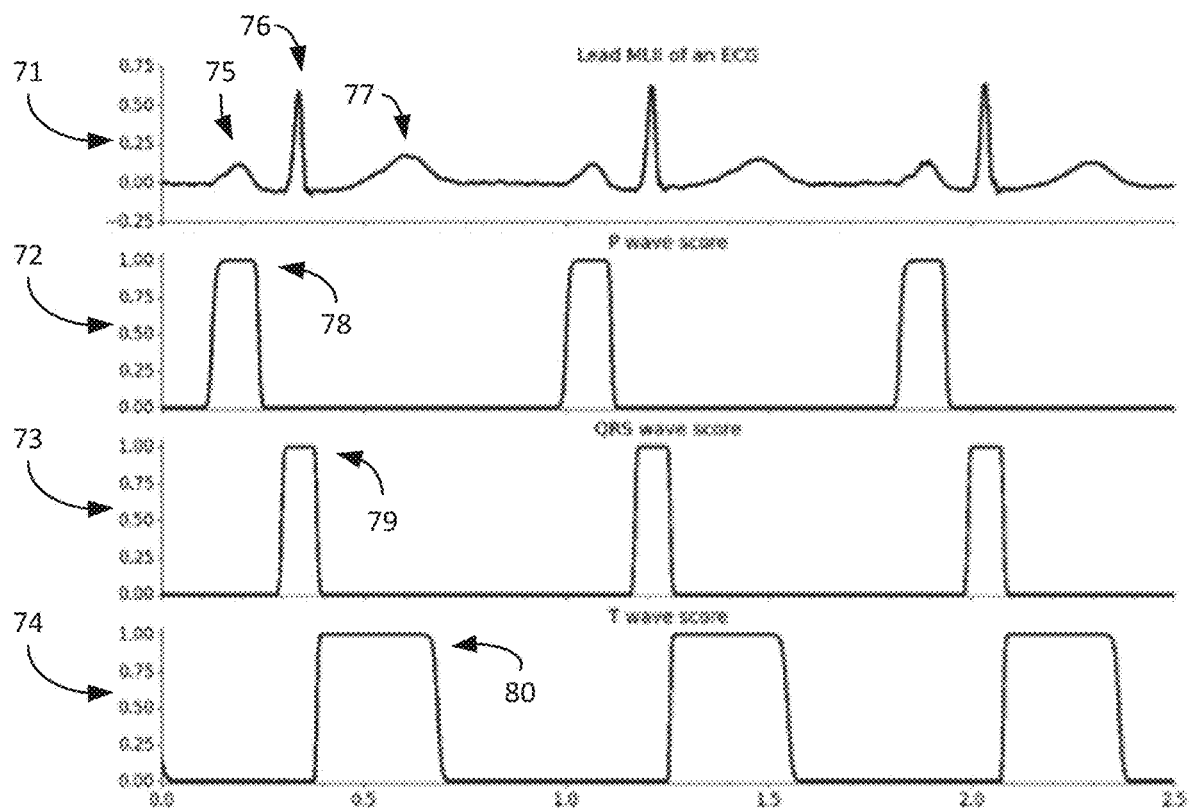
FIGS. 5A-5B are line graphs representing an exemplary ECG signal and an exemplary output of a first neural network for each wave type analyzed, respectively.
Figure 5B:
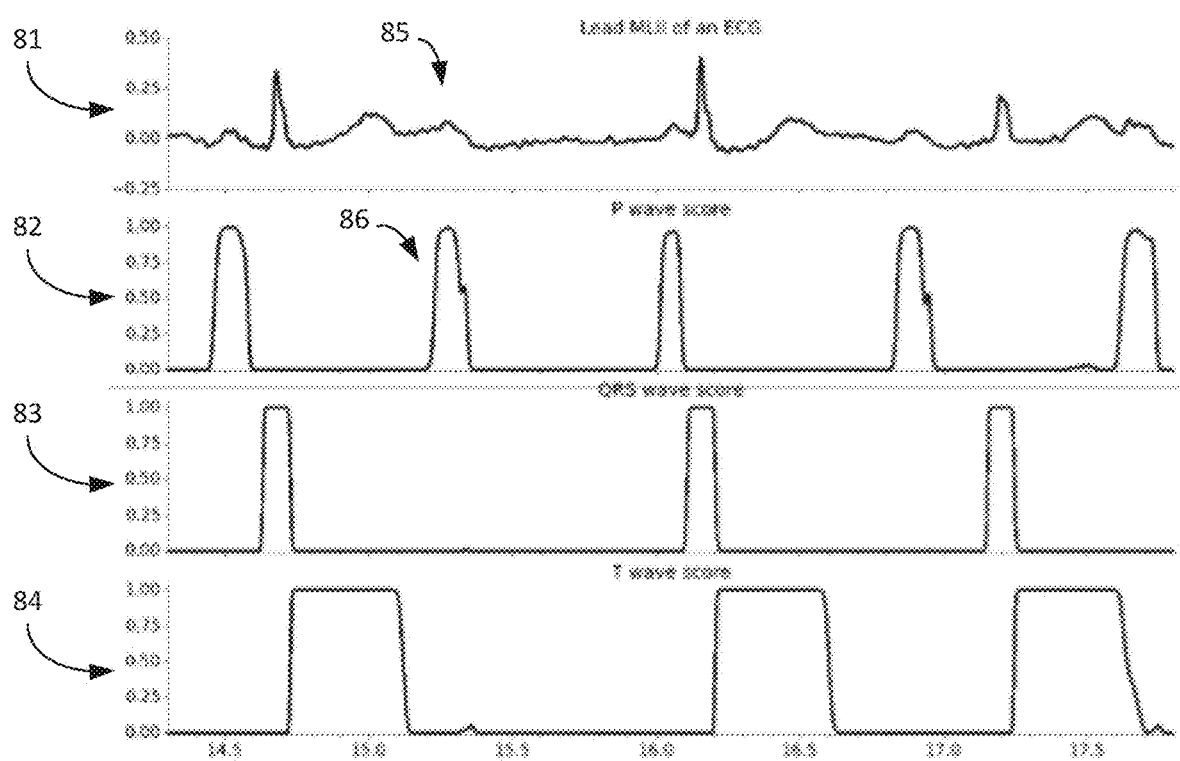

Referring now to FIGS. 5A and 5B, exemplary outputs of the first neural network are graphed for each wave type to illustrate the value of generating scores at each time point corresponding to a plurality of types of waves. Specifically, FIG. 5A illustrates an exemplary output where the delineation neural network processed a normal cardiac signal (with no abnormalities) and FIG. 5B illustrates an exemplary output where the delineation neural network processed a cardiac signal having "hidden" P-waves, for example due to an atrioventricular block.

Referring now to FIG. 5A, four line graphs are illustrated, each graph showing time on the x-axis. Line graph 71 represents the cardiac signal over multiple beats. The plotted signal reflects the well-known ECG waveform having a P-Wave (point 75), QRS complex (point 76), and T-wave (point 77). Line graph 72 is a graph the P-wave score over the same time points in the cardiac signal. Similarly, line graph 73 and line graph 74 are graphs of the QRS score and T-wave scores, respectively, over the same time points. The y-axis for each line graphs 72-74 is the score assigned at each time point, ranging from 0 to 1, with 0 indicating a low likelihood of the presence of a particular wave and 1 indicating a high likelihood of the presence of a particular wave. For example, line graph 72 indicates a very high likelihood of the presence of P-waves at score 78 which corresponds to the time points near point 75, line graph 73 indicates a very high likelihood of the presence of a QRS complex at score 79 which corresponds to the time points near point 76, and line graph 74 indicates a very high likelihood of the presence of a T-wave at score 80 which corresponds to the time points near point 77.

FIG. 5B, like FIG. 5A, illustrates four line graphs, line graphs 81-82, which are similar to line graphs 71-74. Specifically, line graph 81 represents the cardiac signal over several beats, line graph 82 represents the P-wave score over the cardiac signal, line graph 83 represents the QRS score over the cardiac signal, and line graph 84 illustrates the T-wave score over the cardiac signal. Unlike FIG. 5A, the ECG signal in line graph 81 includes hidden P-waves such as the hidden P-wave shown at point 85. Hidden P-waves are P-waves that occur during another wave or complex such as a T-wave. As the cardiac signal processed by the delineation network involves a high sample rate and the delineation network generates data for each wave type at each time point, the output recovered is robust enough (i.e., includes enough sample points) to identify two waves occurring at the same time, such as the case with hidden P-waves. For example, line graph 82 indicates a very high likelihood of the presence of P-waves at score 86 which corresponds to the time points near point 85. Accordingly, it is understood that the delineation neural network is not limited to recovering only one wave at each time point and therefore can identify several waves at any time point. It is further understood that signals from one or more leads may be processed simultaneously by the first neural network.

Using the scores assigned to each time point corresponding to each wave type (e.g., P-wave, QRS complex, T-wave, etc.), delineator 39 may post-process the cardiac signal. Post-processing involves, assigning to each time point, none, one, or several waves, calculating the onset and offset of each of the identified waves, and optionally determining the characterization of the waves. Waves may be assigned to each time point by determining that a wave exists at that time point if a certain value is achieved. Computing the "onset" and "offset" of each wave involves computing the time points of the beginning and the end of each wave in the cardiac signal, the beginning referred to as the "onset" and the end referred to as the "offset." This may involve analyzing the time points corresponding begging and end of the highest values for each wave type. Delineator 39 may characterize the waves by identifying prematurity, conductivity and ectopy. Wave characterization leverages the contextual information between each wave and/or each beat. For example, the premature label may be applied to the wave if a certain threshold value is achieved at a certain time point or an average value over several time points.

After computing the onset and offset of each wave type in the cardiac signal, delineator 39 may calculate global measurements. Global measurements are derived from the onset and offset of each wave type and may relate to features and characteristics of the cardiac signal such as intervals between waves and wave durations. For example, global measurements may include, but are not limited to, PR interval, P-wave duration, QRS complex duration, QRS axis, QT interval, corrected QT interval (Qtc), T-wave duration, JT interval, corrected JT interval, heart rate, ST elevation, Sokolov index, number of premature ventricular complexes, number of premature atrial complexes, ratio of non-conducted P waves, and/or ratio of paced waves.

Delineator 39 may further deduce labels solely from the information generated by delineator 39. For example, the following labels may be deduced by delineator 39: short PR interval (i.e., PR interval<120 ms), first degree AV block (e.g., PR interval>200 ms), axis deviations, long QTc, short QTc, wide complex tachycardia, and/or intraventricular conduction blocks. Labels determined solely from information generated by delineator 39 are referred to as delineation based labels.

Referring again to FIG. 4, ECG platform 37 may cause the output of step 56 (e.g., wave information 62) as well as pre-processed ECG data 55 to be communicated or otherwise applied to clusterer 42 for clustering at step 63. Wave information 62 may include scores regarding PVC waves and PAC waves including onsets and offsets generated and relevant durations. Clusterer 42 may process wave information 62 and identify clusters of PAC or PAV waves during the duration of the cardiac signal. Once identified, clusterer 42 may assign cluster label 64 to one or more time windows, identifying either a PVC or a PAC cluster for each time window. A time window is defined by two time points in the cardiac signal.

Referring again to FIG. 4, ECG platform 37 may also cause the output of step 56 (e.g., wave information 57) as well as pre-processed ECG data 55 to be communicated or otherwise applied to classifier 41 for classification at step 58. Classification at step 58 involves applying a second neural network (i.e., classification neural network) to pre-processed ECG data 55. Accordingly, in one example, the input of the second neural network may be one or more multi-lead cardiac signals with variable length that is pre-processed. Classifier 41 may also process wave information 57 and/or other information such as patient-specific information including the patient's age or any relevant clinical information. As explained above, ECG platform 37 may cause optionally cause pre-processed ECG data 55 to be communicated directly to classifier 41 and processed by classifier 41 if delineation at step 56 is not necessary. In this manner, classifier 41 may process data sampled multiple times per heart beat across a plurality of heart beats.

The second neural network generates an output having values that correspond to the likelihood of the presence of one or more abnormality, condition and/or descriptor at each time point of the cardiac signal. If a time point or time window is determined to correspond to a certain abnormality, condition, and/or descriptor, a label corresponding to that abnormality, condition, and/or descriptor will be assigned to that time point or window. In one example, one or more labels 59 may be assigned to a time point or time window if a score achieves a predetermined threshold. Accordingly, multi-label localization may be achieved for abnormalities, conditions, and/or descriptors by generating a plurality of values at each time point and assigning one or more labels at each time point.

Classifier 41 may recover the output of the classification neural network as a vector of size q. The values in the vector correspond to the presence of each label at each time point or each time window. For example, the output of the classification neural network may be the vector [0.98: 0.89; 0.00] with the corresponding labels for each element of the vector: Right Bundle Branch Bloc; Atrial Fibrillation; Normal ECG. The scores may be between 0 and 1. For the vector above, a threshold of 0.5 would result in the labels "Right Bundle Branch Block" and "Atrial Fibrillation" being assigned by classifier 41 to the time point or time window corresponding to the score. It is understood that the threshold may be preprogrammed and/or selected by the user and may be modified to provide varying degrees of sensitivity and specificity. By assigning one or more labels for each time point, onsets and offsets corresponding to each label may be computed to identify durations of episodes (e.g., abnormalities episodes).

Abnormalities and conditions may include any physiological abnormality or condition which may be identifiable on the cardiac signal. Today about 150 measurable abnormalities may be identified on cardiac signal recordings. Abnormalities and conditions may include but are not limited to, sinoatrial block, paralysis or arrest, atrial fibrillation, atrial flutter, atrial tachycardia, junctional tachycardia, supraventricular tachycardia, sinus tachycardia, ventricular tachycardia, pacemaker, premature ventricular complex, premature atrial complex, first degree atrio-ventricular block (AVB), 2nd degree AVB Mobitz I, 2nd degree AVB Mobitz II, 3rd degree AVB, Wolff-Parkinson-White syndrome, left bundle branch block, right bundle branch block, intraventricular conduction delay, left ventricular hypertrophy, right ventricular hypertrophy, acute myocardial infarction, old myocardial infarction, ischemia, hyperkalemia, hypokalemia, brugada, and/or long QTc. Descriptors may include descriptive qualities of the cardiac signal such as "normal" or "noisy ECG."

Upon applying the second neural network at step 58, classifier 41 may read each time point of the cardiac signal as well as each global measurement, analyze each time point of the cardiac signal and each global measurement, compute time windows by aggregating at least two time points, and compute scores for each time window, the scores corresponding to a plurality of non-exclusive labels.

Figure 6A:
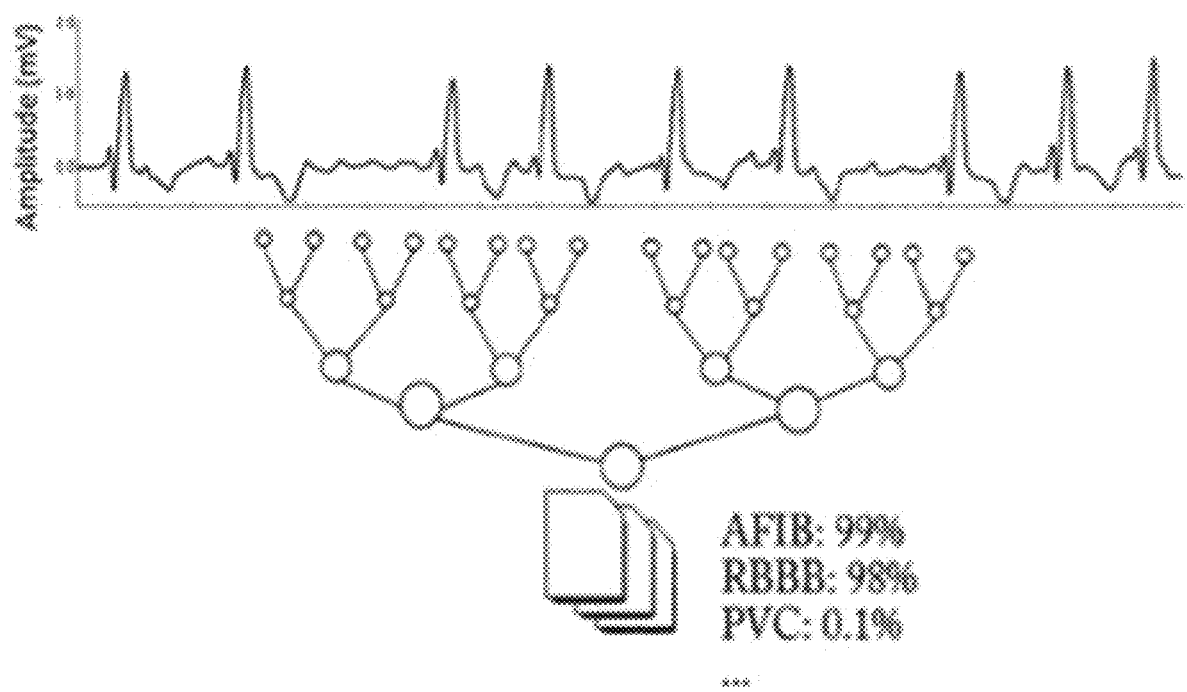
FIGS. 6A-6B are exemplary representations of classification neural networks in the form of a convolutional neural network and a recurrent neural network, respectively.

The classification neural network may be a convolutional neural network or a recurrent neural network. Referring now to FIG. 6A, a classification neural network in the form of a convolutional neural network is illustrated applied to an ECG signal. Most convolutional neural networks implement a few convolutional layers and then standard layers so as to provide a classification. The ECG signal is given as input to the network, which aggregates the information locally and then combines it layer by layer to produce a high-level multi-label classification of the ECG. For each label a score is provided. The labels of the convolutional neutral network shown in FIG. 6 include atrial fibrillation (AFIB), right bundle branch block (RBBB) and, and premature ventricular complex (PVC).

Figure 6B:
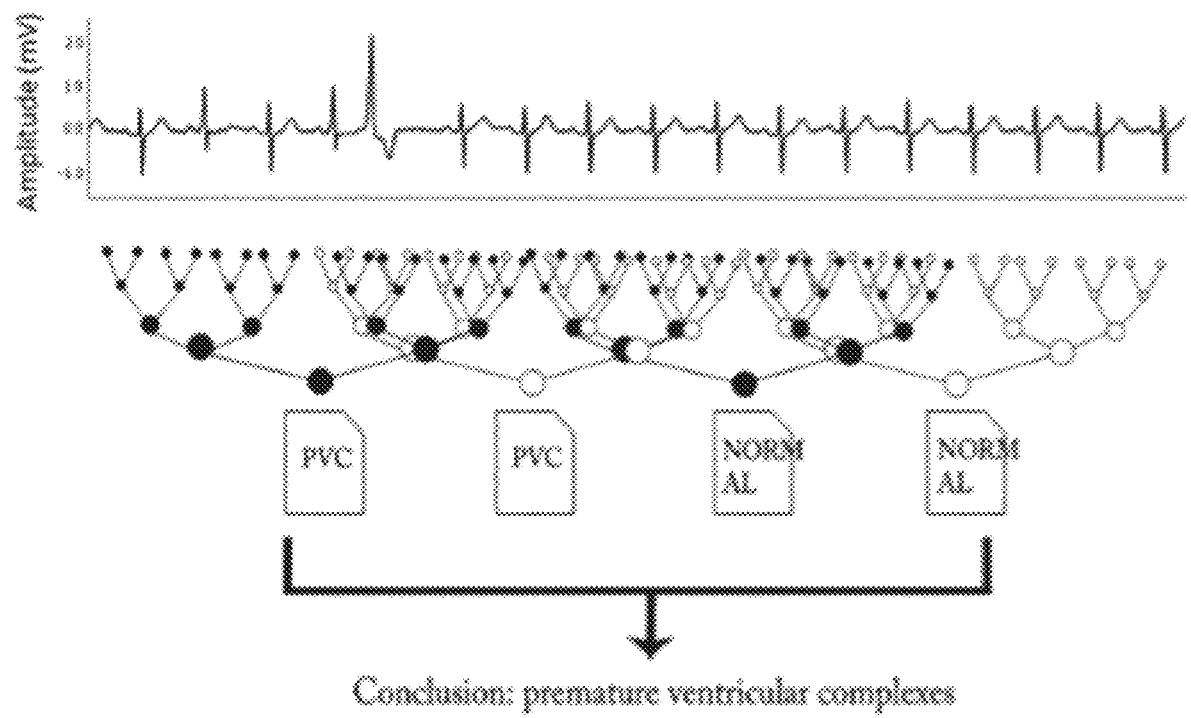

Referring now to FIG. 6B, a classification neural network in the form of a recurrent convolutional neural network is illustrated. Similar to FIG. 6A, the ECG signal is given as input to the network. A recurrent convolutional neural network refers to a particular convolutional neural network structure able to keep memory of the previous objects it has been applied to. A recurrent convolutional neural network is composed of two sub-networks: a convolutional neural network which extracts features and is computed at all time points of the cardiac signal, and a neural network on top of it which accumulates through time the outputs of the convolutional neural network in order to provide a refined output. In this manner, the convolutional neural network acts as a pattern detector whose output will be accumulated in time by the recurrent neural network.

As is shown in FIG. 6B, the output of the convolutional neural network identified four labels at various time points including premature ventricular complex (PVC) and Normal. Those labels were then applied to the second neural network which produced the refined output "premature ventricular complex." In this example, the network correctly recognized a premature ventricular complex (PVC, the fifth and largest beat) in the first part of the signal while the second part of the signal is considered normal. As the cardiac signal includes abnormality, it cannot therefore be considered as normal, and the accumulated output is therefore PVC.

The first neural network (i.e., delineation neural network) and the second neural network (i.e., classification neural network) must be trained to achieve the behavior and functionality described herein. In both the delineation and the classification embodiments, the networks may be expressed using open software such as, for example, Tensorflow, Theano, Caffe or Torch. These tools provide functions for computing the output(s) of the networks and for updating their parameters through gradient descent.

Training the neural networks involves applying numerous datasets containing cardiac signals and known outputs to the neural networks. A database of the datasets containing cardiac signals collected across a plurality of patients using the systems and methods described herein may be stored on server 15 and/or drive 16 (e.g., in the cloud). The datasets in the database may be used by server 15 to analyze new cardiac signals inputted into the system for processing. In a preferred embodiment, any cardiac signal applied to the trained neural network will have the same sampling rate and/or frequency as the cardiac signals in the datasets used to train the neural network. For example, training of the classification neural network begins with a dataset containing cardiac signals and their known delineation. As explained above, the cardiac signal is expressed as a matrix of size m×n at a predefined frequency. For example, the network may be trained at 250 Hz, 500 Hz or 1000 Hz, though any frequency could be used. The delineation is then expressed in the form of a Matrix Y of size p×n where p is the number of types of waves. Each wave is expressed with their start and end points such as, for example: (P, 1.2 s, 1.3 s), (QRS 1.4 s 1.7 s), (T, 1.7 s, 2.1 s), (P, 2.2 s, 2.3 s). In this example, the first row of Matrix Y corresponds to P-waves, and will have a value of 1 at times 1.2 s and 1.3 s, and as well as 2.2 s and 2.4 s, and 0 otherwise. The second row of Matrix Y corresponds to QRS complexes and will have a value of 1 at times 1.4 s and 1.7 s, and otherwise 0. Finally, the third row of Matrix Y corresponds to T-waves and will have a value of 1 at times 2.2 s and 2.3 s, and otherwise 0. The parameters of the network may then be modified so as to decrease a cost function comparing the known delineation and the output of the network. A cross-entropy error function is used so as to allow for multi-labeling (i.e., allowing for multiple waves at a given instant). This minimization can be done though a gradient step, repeating the foregoing steps at least once for each cardiac signal of the dataset. It is understood that a similar approach may be used to train the delineation neural network (i.e., second neural network).

Figure 7:
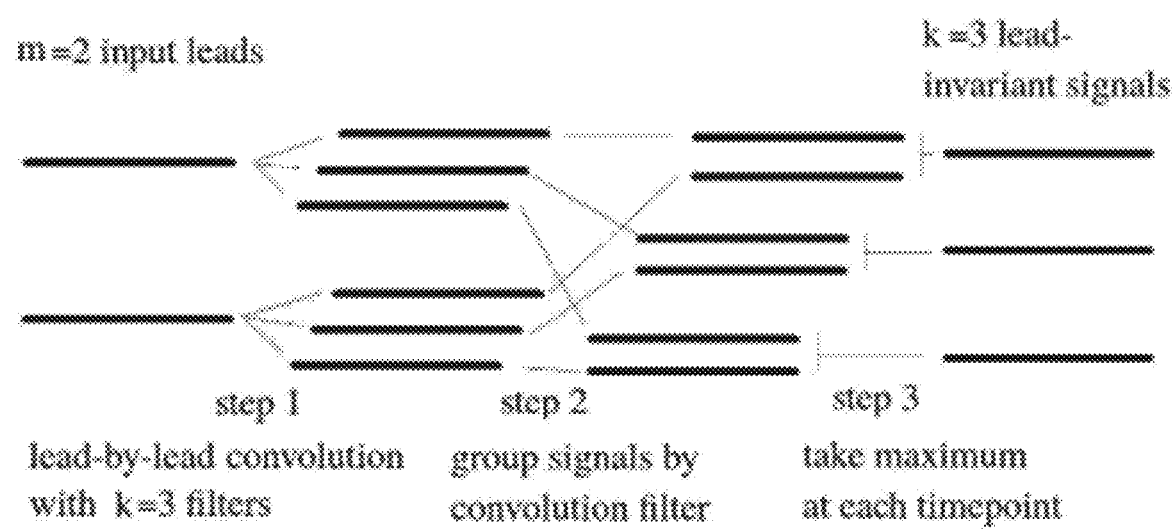
FIG. 7 is an exemplary representation of a variable number of lead entries and a constant number of outputs.

It is further understood that ECG platform 37 may cause neural networks described herein to process cardiac signals having a differing number of leads in entry. For example, the neural network may comprise a sequence of layers at the beginning of the network so as to obtain a network which is independent of the number of input leads and can therefore process cardiac signals with any number of leads m. For example, FIG. 7 illustrates two input leads (m=2) and three output signals (k=3). However, the same structure can process any number of input leads m and will still provide the same number of output signals, which can be fed to the rest of the network for which a fixed number of input signals is required. For this reason, the number of input leads may vary and need not be fixed.

As is shown in FIG. 7, to obtain k signals from an m input leads, the leads may be convoluted using a lead-by-lead convolution with k filters. The signal may then be grouped by a convolution filter in order to obtain k groups of m leads and a mathematical function is finally applied to each group to obtain k leads. The mathematical function may be the maximum at each time point or may be any other function known to one skilled in the art.

Referring again to FIG. 4, at step 61, ECG platform 37 may cause labels for each time window (i.e., labels) to be aggregated by post-processor 43 to generate processed labels 60. The labels may be derived from global measurements based on delineation. For example, the label corresponding to first degree atrioventricular block may be derived from a PR interval longer than 200 ms. As explained above, the PR interval is a global measurement based on the delineation. Post-processor 43 may also aggregate the delineation-based labels with the classification labels corresponding to the same time points.

Post-processor 43 may also filter the labels to remove redundant labels, assemble labels according to a known hierarchy of labels, or ignore labels that are known to be of lesser importance according to a hierarchy or weighted values. Post-processor 43 may also aggregate the labels through time so as to compute the start (onset) and end (offset) times of each abnormality. It is understood that post-processor 43 may be a standalone component or may be a subcomponent of classifier 41.

As is shown in FIG. 4, the information generated on back end 46 by ECG platform 37 in steps 54, 56, 58 and 61, and optionally, 63, may be communicated by ECG platform 37 to ECG application 29 on front end 45. ECG application 29 may cause the foregoing information to be displayed on display 17 of system device 14. The information generated on back end 46 may be automatically transmitted by ECG platform 37 or ECG platform 37 may cause the information to be stored on server 15 until requested by ECG application 29. Upon generating the data, ECG platform 37 may transmit a message to ECG application 29, informing ECG application 29 that the data is available from ECG platform 37.

ECG application 29 may receive data (e.g., raw ECG data, pre-processed ECG data, wave information, labels and any other data generated during steps 54, 56, 58, 61, and/or 63) and cause system device 14 to display as described in PCT/EP2018/072912, the entire contents of which are incorporated herein by reference. Specifically, the '912 application explains that the ECG signal, features of the ECG signal, and/or descriptors of the ECG signal may be displayed in a multiple field display in an interactive manner.

Figure 8:
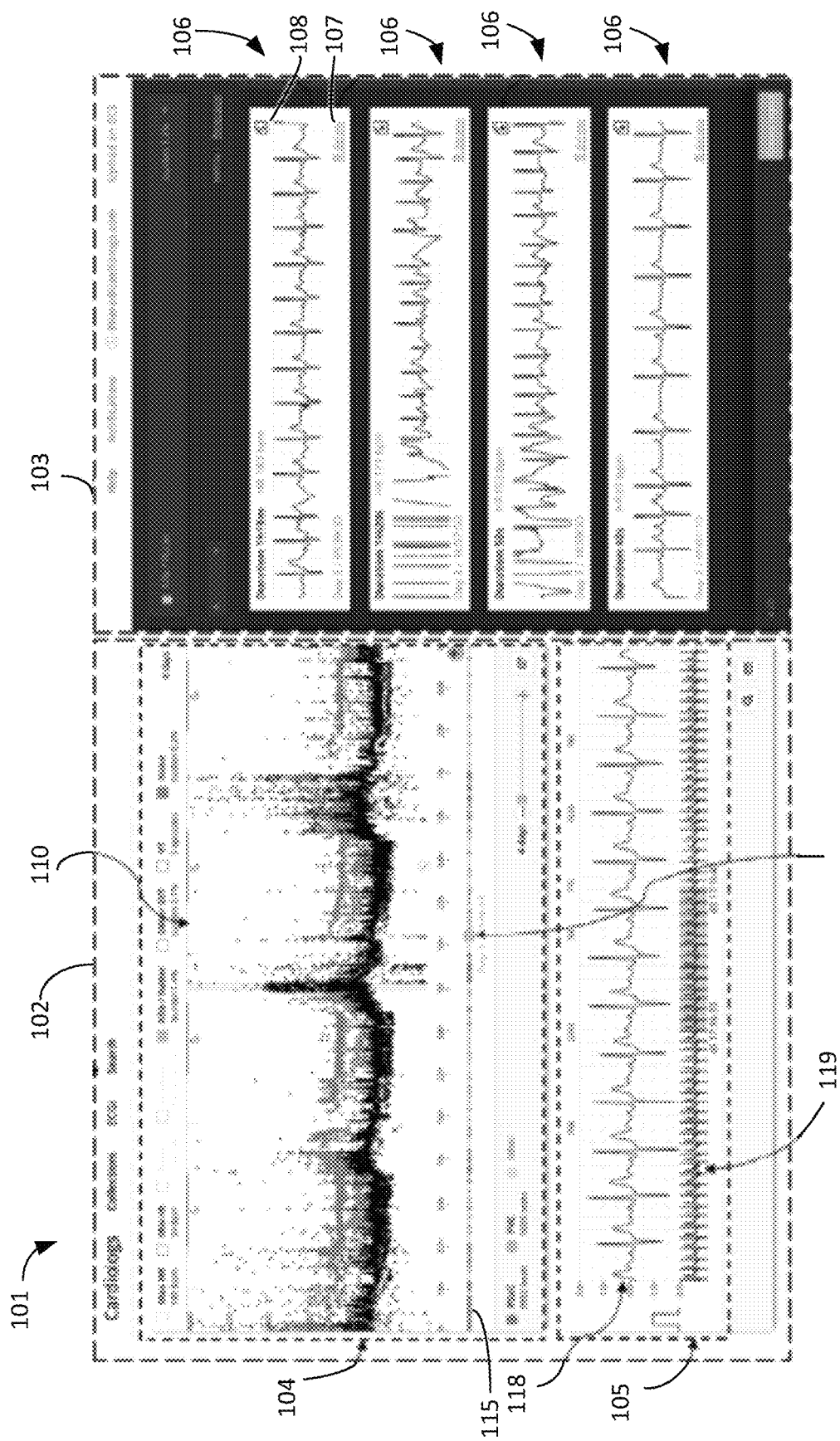
FIG. 8 is an exemplary user interface having an R-R plot generated in accordance with aspects of the resent disclosure.

Referring now to FIG. 8, an exemplary display, interactive display 101, is illustrated. Interactive display 101 includes first side 102 and second side 103. First side 102 further includes second graphic window 105 and first graphic window 104, having plot 110 which includes data corresponding to the ECG signal. First graphic window 104 includes plot 110 providing a global view of an ECG signal.

Figure 9:
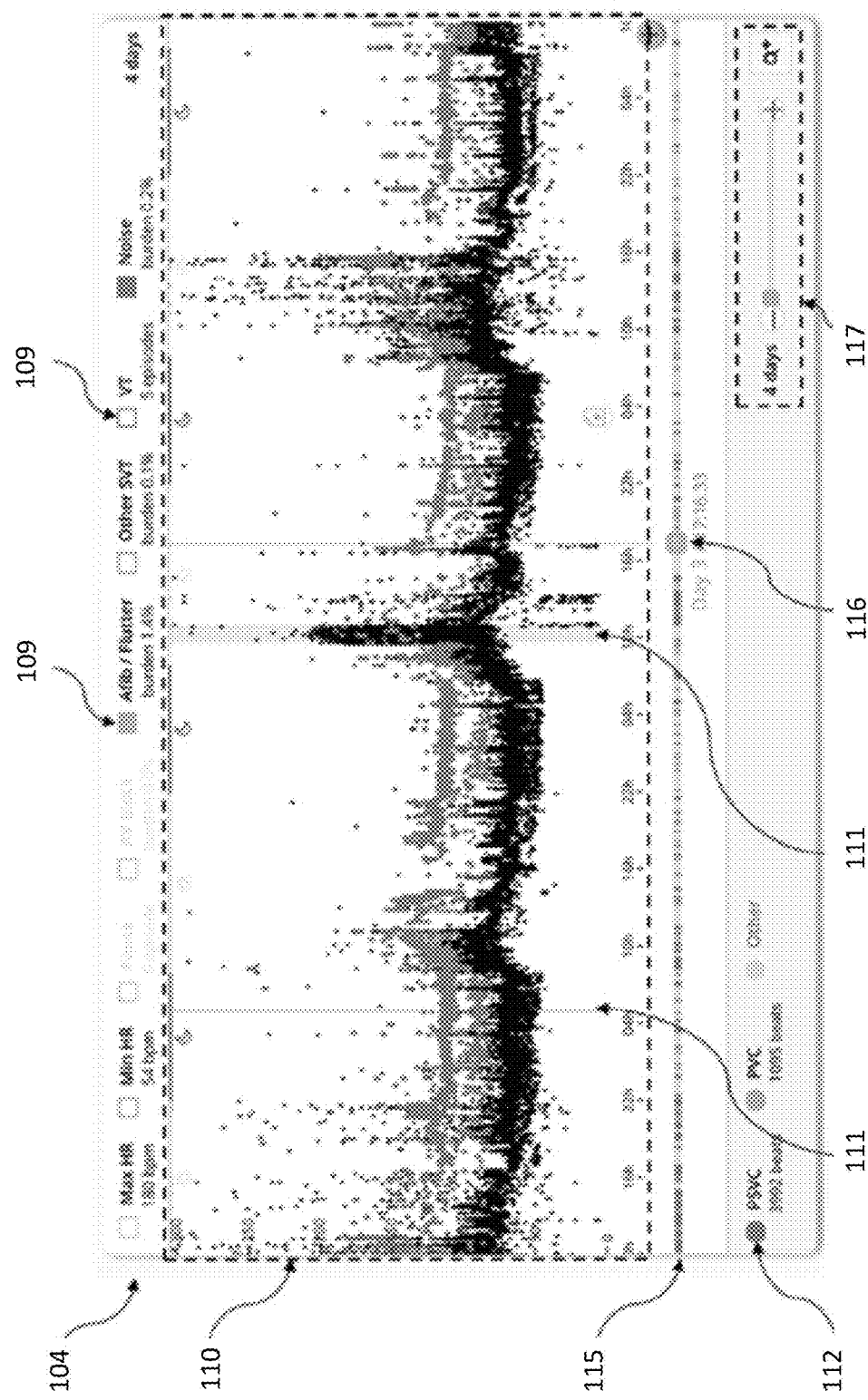
FIG. 9 is a zoomed-in view of the R-R plot shown in FIG. 8.

Referring now to FIG. 9, a zoomed-in version of first graphic window 104 is illustrated. In this exemplary display, plot 110 is an R-R interval plot which is a plot of R-R intervals (interval between two QRS waves) through time. As shown in FIG. 9, the upper region of first graphic window 104 comprises multiple label buttons 109. Each label button 109 has, displayed in its proximity, text describing the label to which it is associated. Each label button 109 is associated with a color so that, when label button 109 is selected by the user, graphic portion 111 is displayed on the plot 110 to visually indicate the presence the episodes and/or events corresponding to the label associate with label button 109. This provides visual references for the user permitting easy identification of a specific category of events and/or episodes along the cardiac signal. In the exemplary display illustrated in FIG. 9, secondary labels 112 are included. In this exemplary display, secondary labels 112 include beat label PVC (premature ventricular complex) and PSVC (premature supraventricular complex), though it is understood that other secondary labels may be included. The points in the plot 110 associated with the label PVC and PSVC are colored, as shown in FIG. 9 by the presence of points of color different from black.

First graphic window 104 further comprises, parallel to the time axis of the plot 110, temporal bar 115. Temporal bar 115 provides a linear representation of the total ECG acquisition time wherein the time periods associated to episodes or events are represented as colored segments. As is shown in FIG. 9, the darker grey zones on temporal bar 115 correspond to time periods of noisy signal (e.g., when the signal is too artifacted and the analysis algorithm cannot propose a delineation and proper detection). First graphic window 104 further comprises interactive cursor 116. A user using ECG application 29 may move interactive cursor 116 along temporal bar 115 to allow a navigation of the plot 110 along the total ECG acquisition time. In the right bottom corner of first graphic window 104, first graphic window 104 comprises second interactive means 117 configured to cause plot 110 to zoom in and out.

Referring again to FIG. 8, second side 103 includes multiple episode plots 106. Each episode plot 106 displays at least one segment of the ECG strip corresponding to a detected episode and may include text regarding the duration (e.g., "Duration: 1 h38 m") and/or the starting time of the episode (e.g., "Day 3/09:39:30"). Each episode plot 106 includes third interactive icon 108 to select the corresponding episode plot for inclusion in a report. Each episode plot 106 further includes fourth interactive icon 107 which permits the user to remove the respective ECG plot from interactive display 101. Second side 103 may further include text describing one or more of episode plots 106.

Interactive display 101 further includes graphic window 105 including ECG strip 118 in a second time window starting at the time point selected by the cursor 116. Second graphic window 105 further includes ECG strip 119 in a third time window which is larger than the second time window which is inclusive of the second time window. The third time window includes a shaded portion which corresponds to the second time window.

Figure 10:
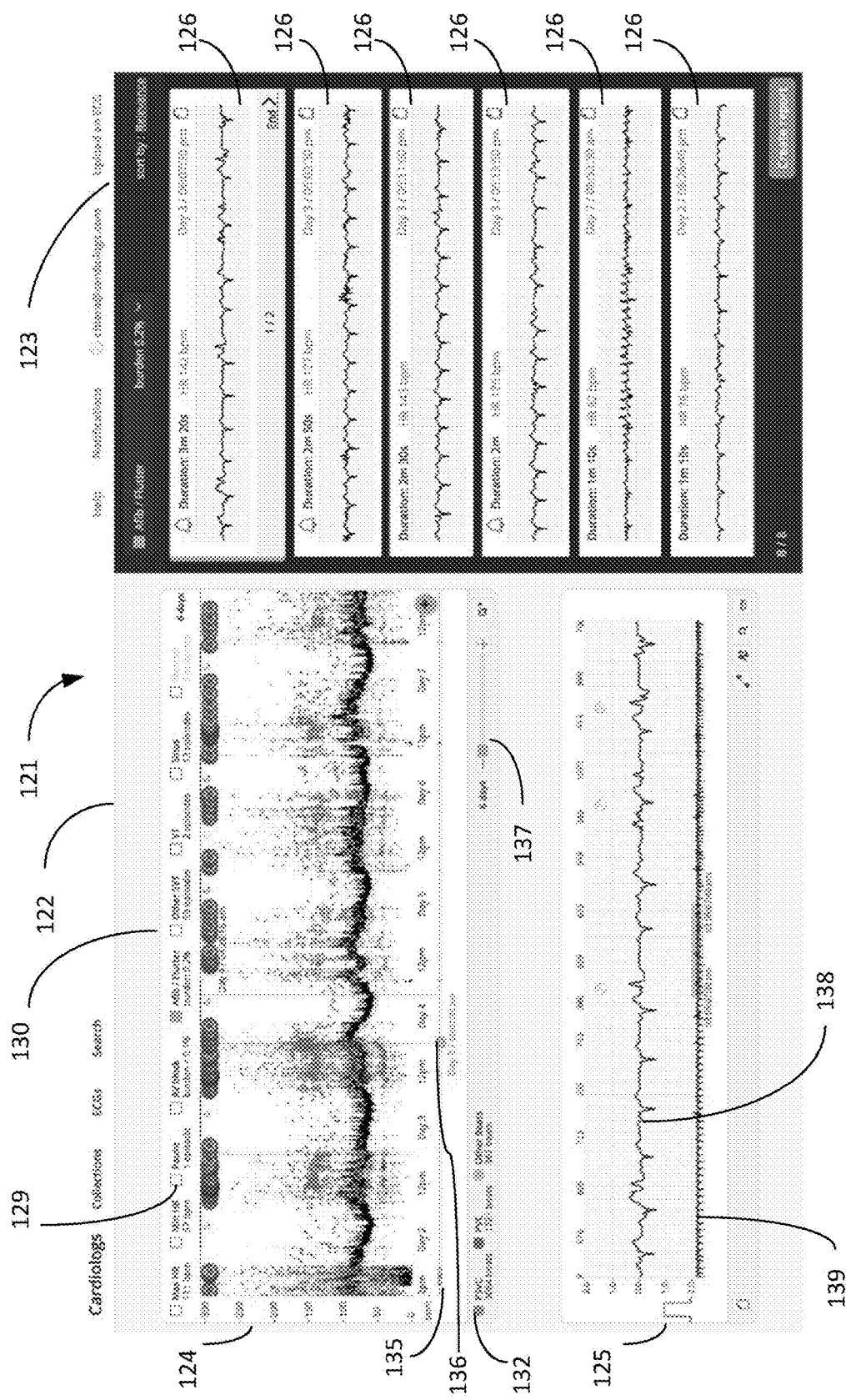
FIG. 10 is an exemplary user interface having a heart rate density plot generated in accordance with aspects of the present disclosure.

Referring now to FIG. 10, a similar display, interactive display 121, is illustrated. Interactive display 121 includes first side 122 and second side 123. First side 122 further includes first graphic window 124 and second graphic window 125. Second side 113 has the same functionality as second side 103 described above, and includes episode plots 126 similar to episode plots 106. Further, second graphic window 125 has the same functionality as second graphic window 105, and includes ECG strip 138 and ECG strip 139 similar to ECG strip 118 and ECG strip 119.

First graphic window 124 is similar to first graphic window 104 except for plot 130. Like first graphic window 104, first graphic window 124 includes multiple label buttons 129 having the same functionality as multiple label buttons 109, secondary labels 132 having the same functionality as secondary labels 112, temporal bar 135 and curser 136 having the same functionality as temporal bar 115 and cursor 116, and second interactive means 137 having the same functionality as second interactive means 117. Unlike plot 110, plot 130 is a heart rate density plot which is the projection onto a bivariate intensity plot of the histogram of the density of heart rates as a function of time.

Figure 11:
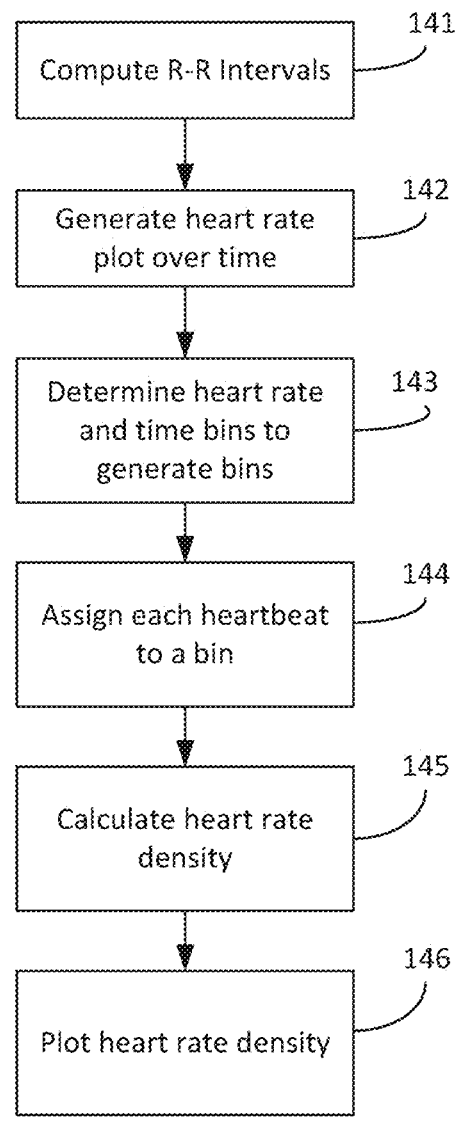
FIG. 11 is a flow chart illustrating an exemplary approach for generating a heart rate density plot.

Referring now to FIG. 11, steps for generating and plotting a heart rate density plot, such as plot 130, are provided. At step 141, ECG platform 37 computes R-R intervals in the cardiac signal (i.e., ECG data). For example, ECG platform 37 may apply the cardiac signal to the delineation neural network to determine the RR intervals, as described above. At step 142, ECG platform 37 may generate the heart rate plot over time. An exemplary heart rate plot, HRDP 150, is illustrated in FIG. 12.

Figure 12:
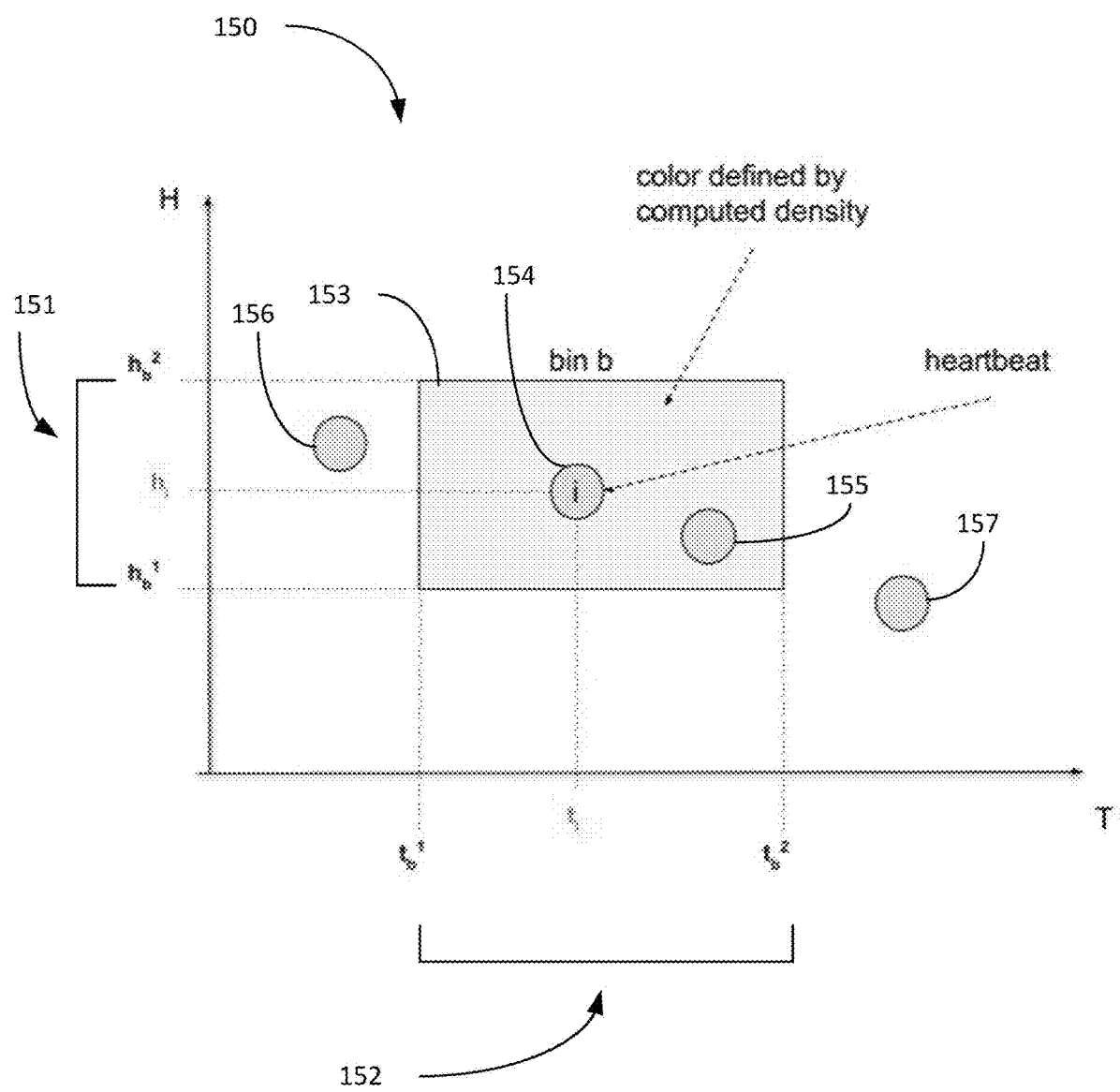
FIG. 12 is an exemplary heart rate density plot generated in accordance with aspects of the present disclosure.

As is shown in FIG. 12, time is projected along the x-axis and the heart rate (e.g., beats per minute) is projected along the y-axis. In one embodiment, both time and heart rate are scaled linearly. However, time and/or heart rate may be scaled logarithmically or using other well-known scales. For simplicity, only four heart beats are shown in FIG. 12.

Referring again to FIG. 11, at step 143, ECG platform 37 may cause the y-axis and the x-axis may be divided into elementary elements, referred to as HR bins and time bins respectively. For example, in FIG. 12, HR bin 151 and time bin 152 are illustrated. HR bin 151 is defined by a first and second heart rate value (e.g., $h_b^1$ and $h_b^2$). Similarly, time bin 152 is defined by a first and second time value (e.g., $t_b^1$ and $t_b^2$). The intersection of a HR bin and a time-bin will be referred to as a bin. In other words, a bin will be defined by a first and second heart rate value and a first and second time value. In FIG. 12, bin 153 is illustrated and defined by HR bin 151 and time bin 152.

Referring again to FIG. 11, at step 144, ECG platform 37 will cause each heartbeat to be assigned to a bin. Specifically, a heartbeat (e.g., QRS complex) that occurs during a time window of a given time bin is included in the computation of the column corresponding to that time bin. Further, a heart rate corresponding to that heartbeat determines which HR bin it belongs to in the column defined by the time bin. For example, in FIG. 12, heartbeat 154 and heartbeat 155 each have a corresponding time and heart rate value that fall within time bin 152 and HR bin 151, respectively. Conversely, heartbeat 156 and heartbeat 157 each have a time value that falls outside time bin 151 and thus neither are included in bin 153.

Referring again to FIG. 11, at step 145, ECG platform 47 will calculate the heart rate density for each time bin. For a given bin, the area defined by the respective time bin and heart rate bin will be represented according to the density of the heart beats comprised in the bin (i.e., number of heartbeats within the bin). Each bin may then be color coded according to the density. For example, each bin may have certain shades of colors or patterns, such as grey levels, for example. In the example in FIG. 12, bins may be represented as levels of grey that get darker as the density of heart rates increases. As is shown in FIG. 12, bin 153, which includes 2 heartbeats, may be represented by a darker shade of grey than a bin with only 1 heartbeat, but a lighter shade of grey than a bin having 3 or more heartbeats.

In a preferred embodiment, the density is calculated as a function of the number of R-waves in the bin divided by the heart rate of the HR bin (e.g. the mean of the minimum and maximum bounds of the time window). This preferred computation of density considers the time spent in a specific bin. For example, in a time bin of 3 minutes, if there occurs 100 beats at a heart rate of 50 bpm (beats per minute) in a first HR bin and 100 beats at 100 bpm in a second HR bin, there will be as many beats in each bin, but 2 minutes will be spent at 50 bpm and only one minute at 100 bpm. Therefore, this bin would have the same density representation if only the number of beats are considered. However, when considering the count of beats divided by the heart rate, the first bin corresponding to the heart rate bin of 50 bpm will be darker than the bin corresponding to the heart rate bin of 100 bpm, as dividing by the heart rate gives higher weight to lower heart rate values. The preferred embodiment therefore captures this temporal information better than only considering the count of beats.

Referring again to FIG. 11, at step 146, ECG platform 37 will plot the heart rate density for each bin. It is understood that capturing temporal information in the column (time bin), in addition to the temporal information naturally given as function of the x-axis, facilitates expression of the density in a manner superior to other forms of aggregated representations of the ECG signal, such as the R-R plot in plot 110.

Figure 13:
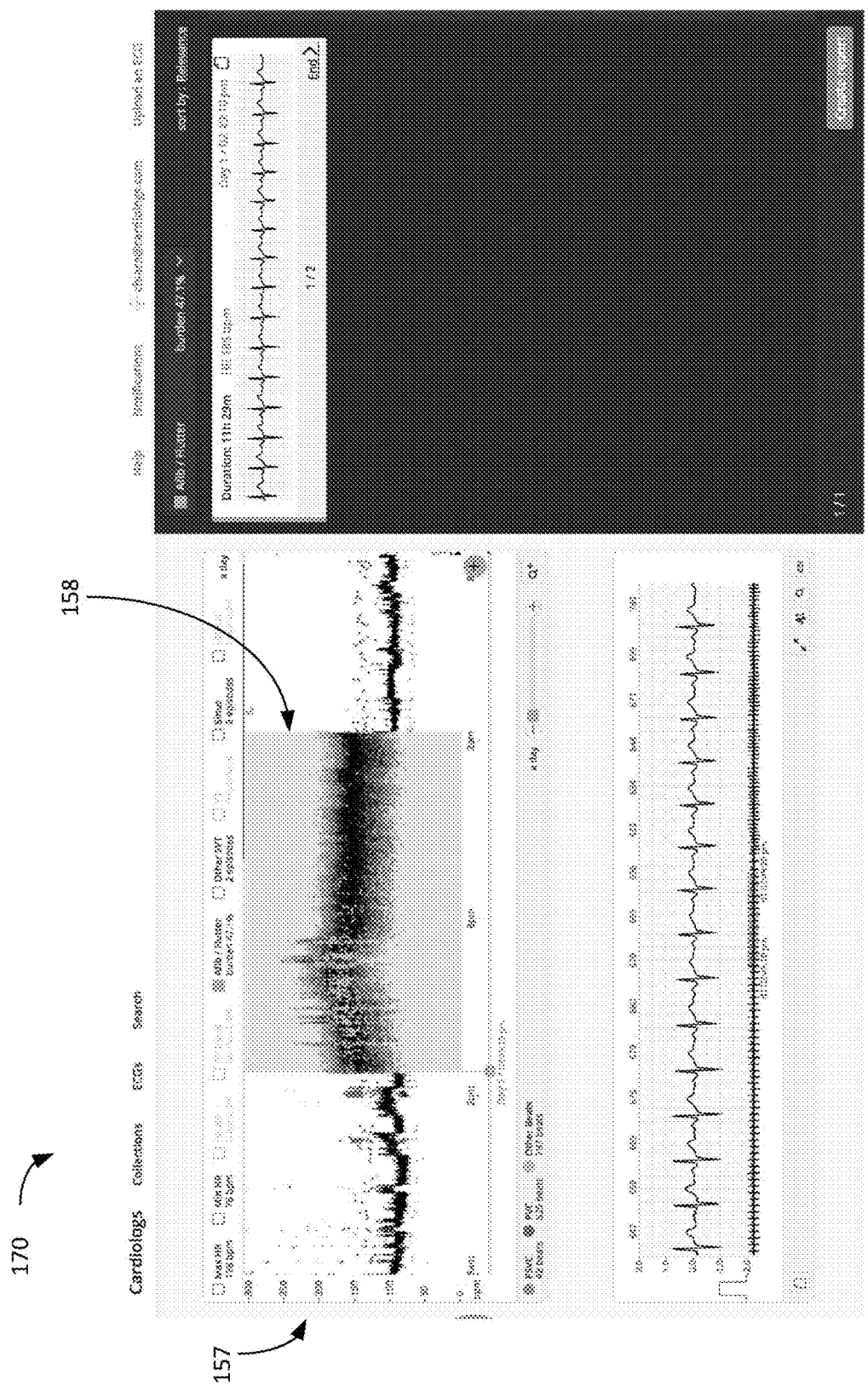
FIG. 13 is an exemplary user interface having a zoomed-in heart rate density plot.

It is understood that the bounds of the x-axis of the HR density plot may be the beginning and end of the signal. However, in a preferred embodiment, the bounds of the x-axis may interactively vary with the action of zooming in and out performed by the user. The bounds of the y-axis remain fixed when performing this action. Referring again to FIG. 10, plot 130 includes interactive means 137 which may be used to zoom-in on the heart rate density plot. The zoom action may only change the size of the plot display. Alternatively, zooming in and out changes the size of the time window corresponding to a time-bin. With the zooming-in action, a bin represented with the same number of pixels covers a shorter time window. Zooming in therefore causes a new computation of the histogram with finer temporal divisions, and consequently, finer temporal information. This allows for a representation of the ECG signal that shows varying levels of aggregation of the information as a function of the time scale one chooses to display, in order for the histogram to remain both readable and informative at any level of zoom. Referring now to FIG. 13, an interactive display, interactive display 170, is illustrated which is similar to the interactive display in FIG. 10. Interactive display 170 has been zoomed-in resulting in plot 159 having zoomed in portion 158.

Figure 14A:
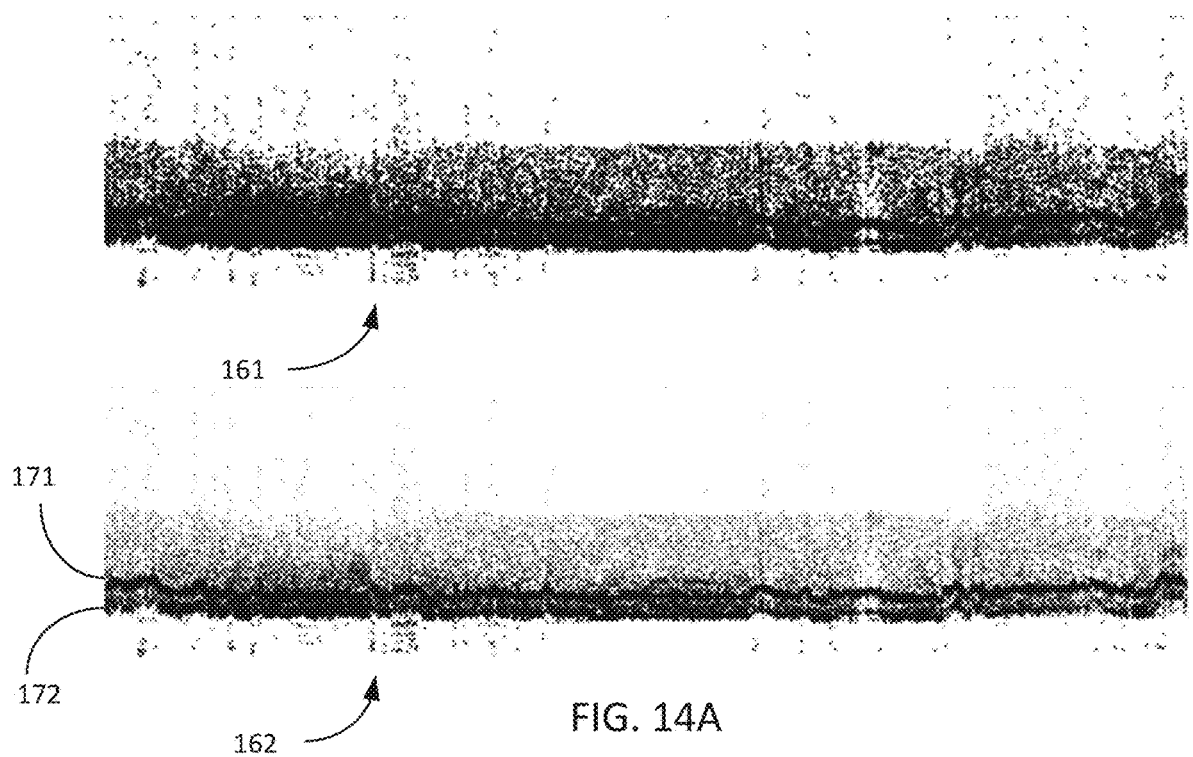
FIGS. 14A-14E are side-by-side comparisons of various R-R plots and heart rate density plots generated from the same cardiac signal.
Figure 14B:
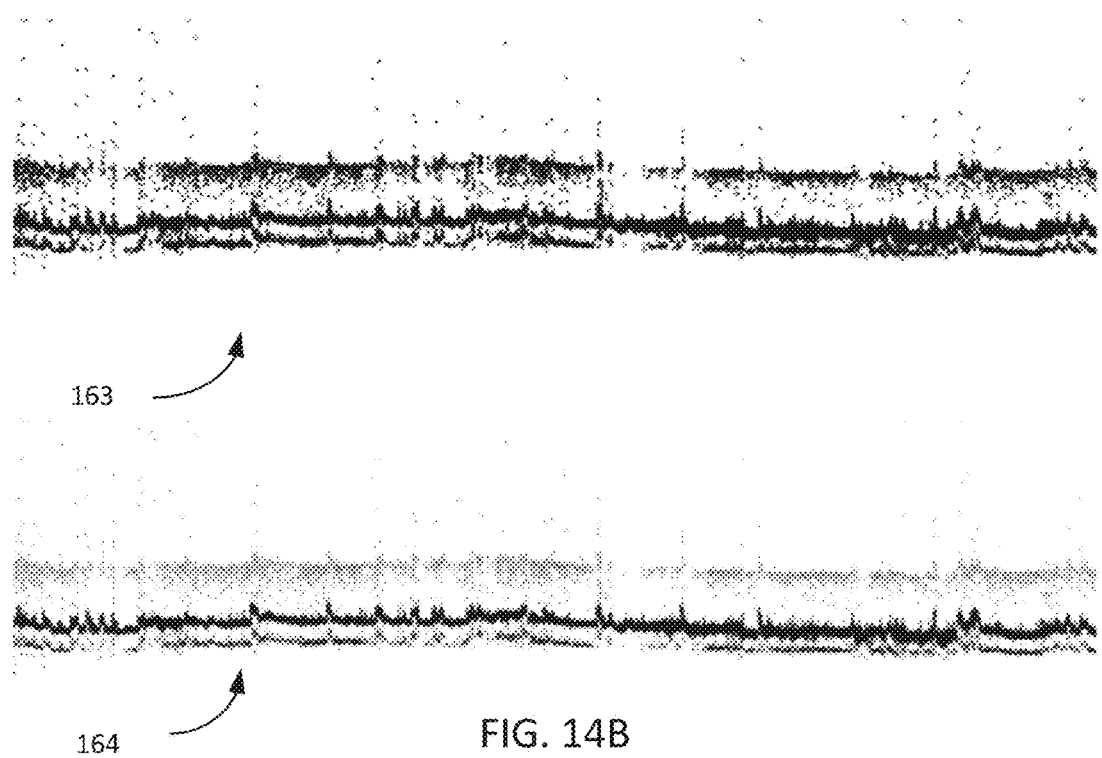
Figure 14C:
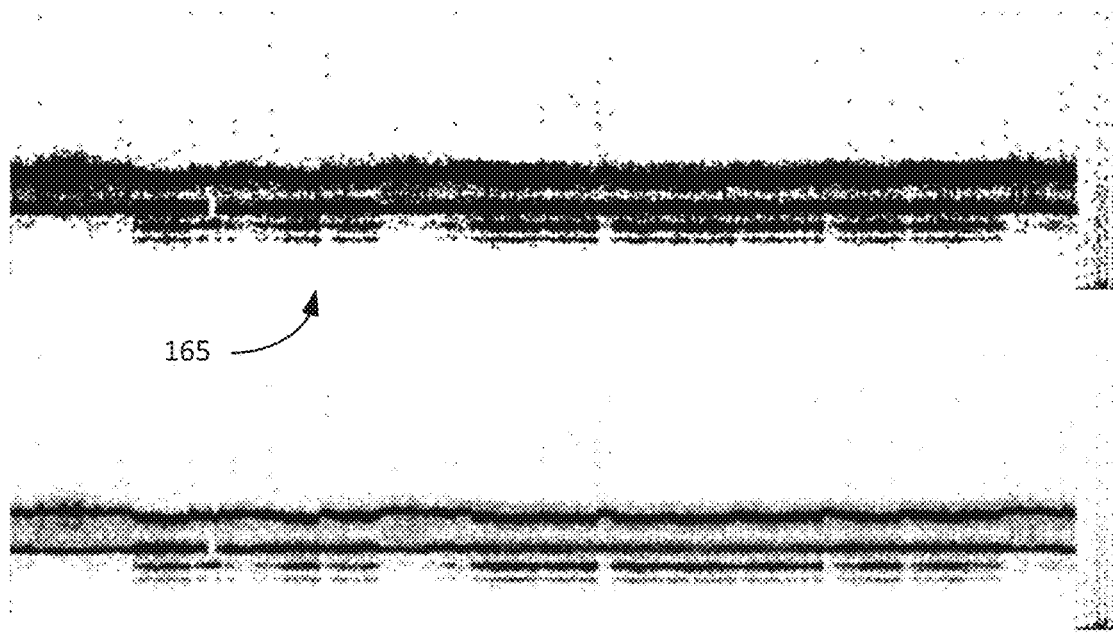
Figure 14D:
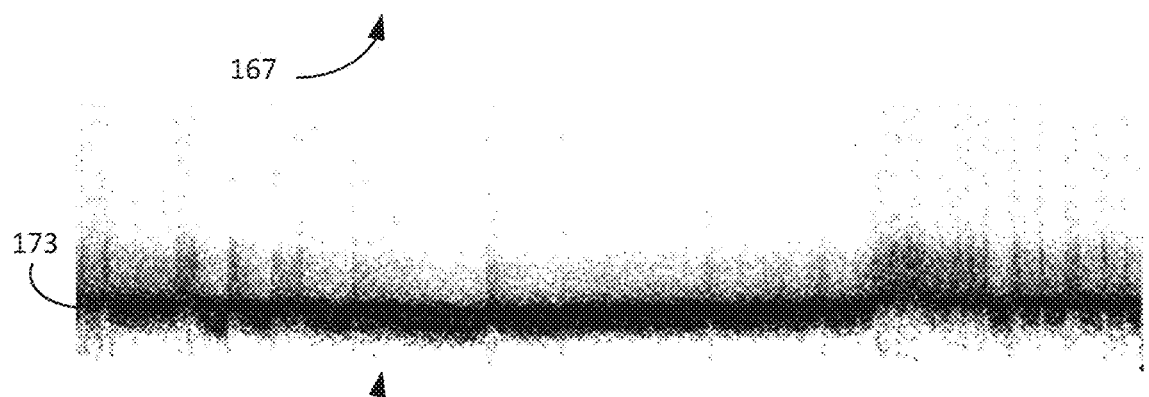
Figure 14E:
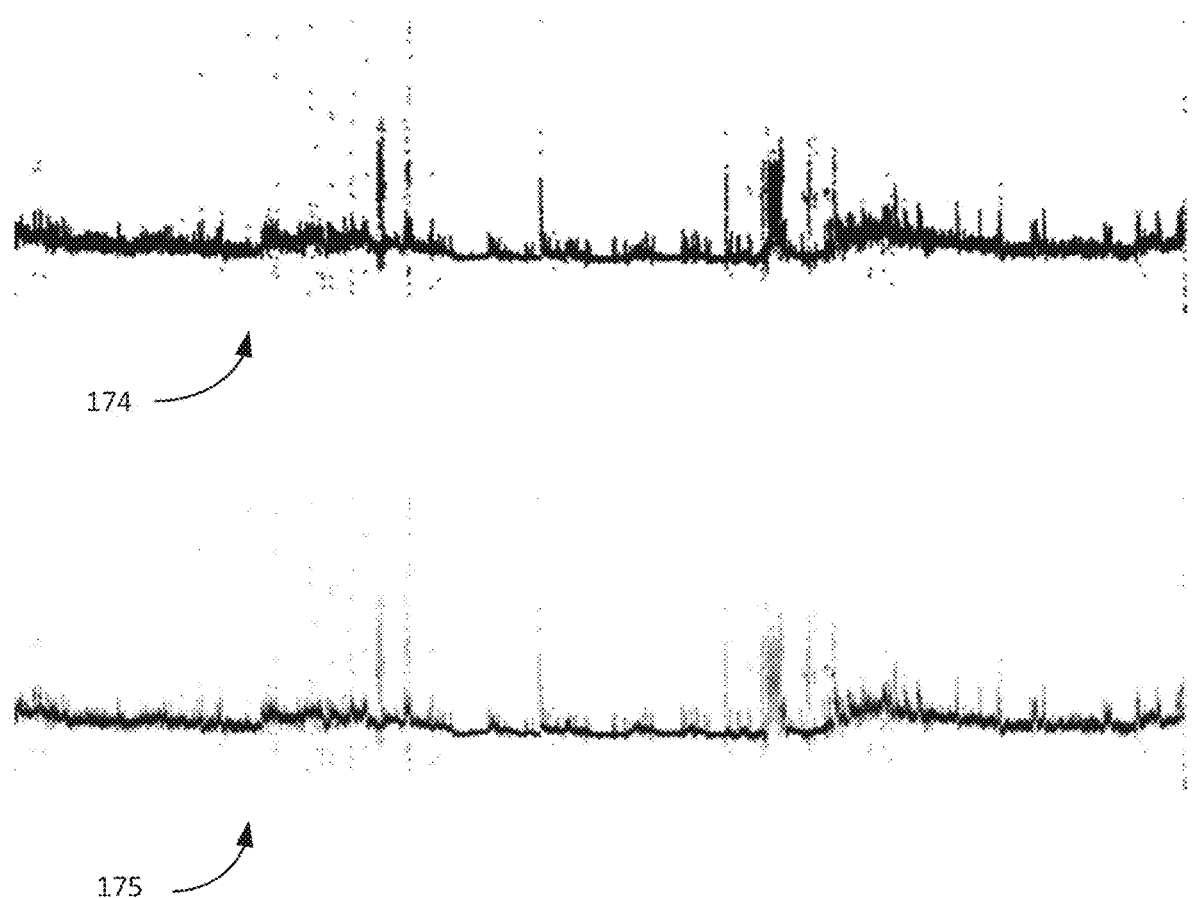

FIGS. 14A-E illustrate the superiority of the HRDP over the typical R-R plot. Referring now to FIG. 14A, a signal generated by a holter having a very high number of PVCs with varying coupling is illustrated as RR plot 161 and density plot 162. In density plot 162, the underlying rhythm is clearly visible as line 171. Further, the compensatory rest is illustrated as line 172 at the bottom. In R-R plot 161, this pattern is less clear. Referring now to FIG. 14B, a signal generated by a holter having less premature complexes than the one in FIG. 14A is illustrated as R-R plot 163 and density plot 164. The main rhythm is clearly illustrated in density plot 164 and is less clear in R-R plot 163. Referring now to FIG. 14C, a signal generated by a holter with vary conduction flutter is illustrated as R-R plot 165 and density plot 166. As is shown in FIG. 14C, the conduction flutter is more emphasized by the four clear black lines in density plot 166 than the four diffuse clouds that appear in the R-R plot 165. Referring now to FIG. 14D, a signal generated by a holter with permanent atrial fibrillation is illustrated as R-R plot 167 and density plot 168. As is shown in this figure, density plot 168 gives more precise information on the variations of the heart rate within the fibrillation. Specifically, darker lower half 173 shows that more time is spent at a low heart rate than at a high heat rate. Density plot 168 further illustrates spikes where the upper half becomes a bit darker corresponding to the heart rate increasing. These nuances are not visible in R-R plot 167. Referring now to FIG. 14E, a signal generated by a holter having paroxysmal atrial fibrillation and otherwise regular rhythm is illustrated as R-R plot 174 and density plot 175. The pattern of a regular rhythm is more visible in density plot 175 where a clear black line emerges. Also, the pattern of atrial fibrillation contrasts more in density plot 175 than R-R plot 174 as the color changes as well (density diminishes which makes the plot lighter).

Referring again to FIG. 4, at step 66, a user using ECG application 29 may interact with an interactive active display described above using input devices 25 to request a report and/or customize the report. A report typically includes portions of the cardiac signal and may involve information pertaining to abnormalities and/or episodes (e.g., episode plots) and/or other information generated during pre-processing (step 54), delineation (step 56), classification (step 58), clustering (step 63) and/or post-processing (step 61). A report may further include patient specific medical data such as the patient's name, age, health history, and/or other medical information. It is understood that any individually identifiable health information, and/or protected health information may be encrypted when communicated between ECG application 29 and ECG platform 37.

As explained above, interactive icons in interactive displays may be engaged to incorporate data and images displayed in a report. For example, third interactive icon 108 may be selected by a user using ECG application 29 to include the corresponding episode plot in a report. Accordingly, at step 66, the user may request a report and may select customized features such as certain data to be included in the report (e.g., abnormality data, episode data, episode plots, etc.).

At step 67, ECG application 29 may transmit the request for a report and selected customizable features (e.g., ECG data to be included in the report) to ECG platform 37 and ECG platform 37 may receive the request and information. ECG platform 37 may log the request and save the information received from ECG application 29. At step 68, ECG platform 37 may cause report generator 44 to generate a report according to the information received from system ECG application 29.

Figure 15A:
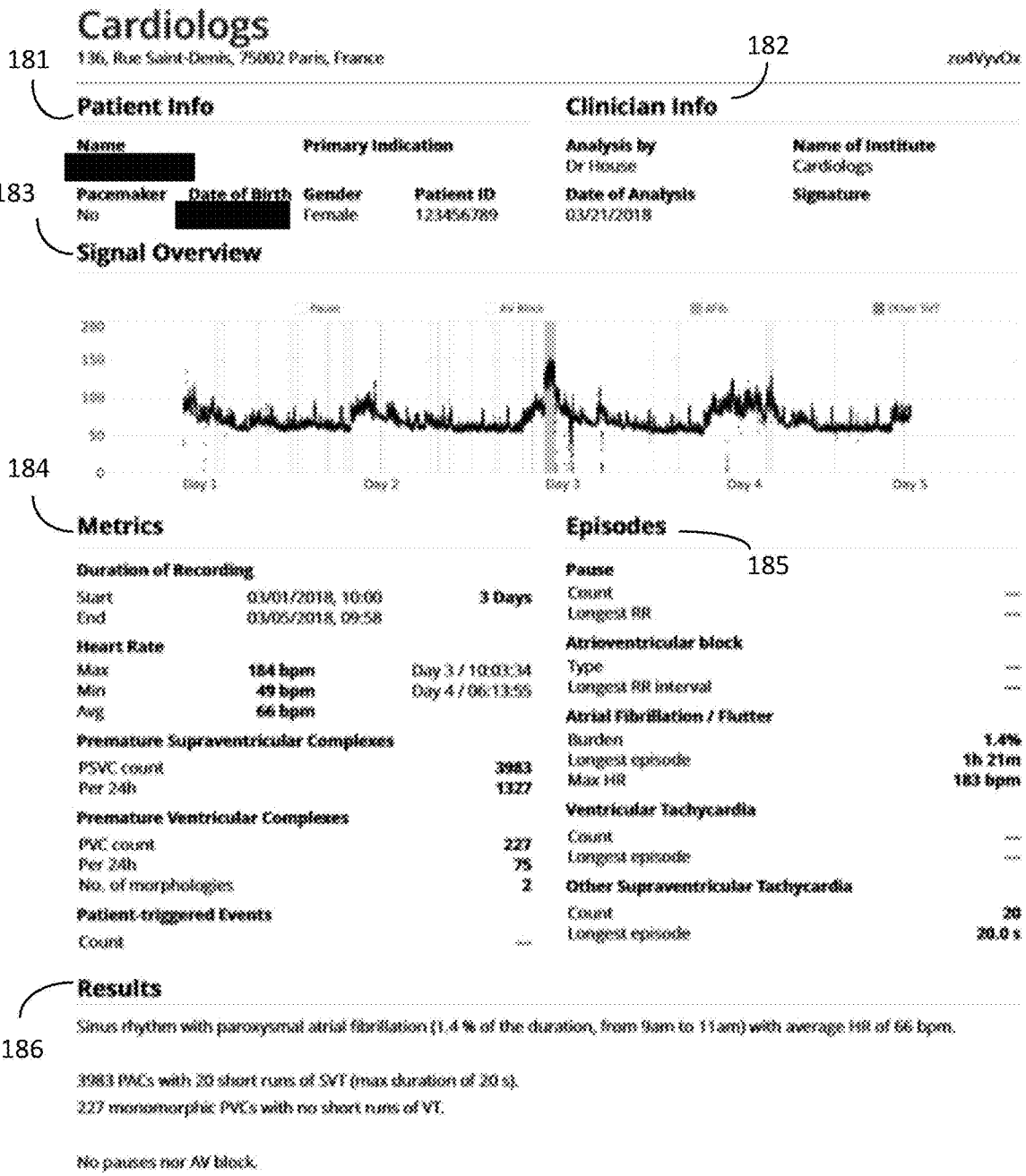
FIGS. 15A-15D is an exemplary report generated by the ECG processing system having information corresponding to the patient and processed ECG data and displaying a heart rate density plot and ECG strips.

Referring now to FIGS. 15A-15D, an exemplary report generated at step 68 is illustrated. The first page of the exemplary report is illustrated in FIG. 15A. The first page may be presented in several sections such as first section 181, second section 182, third section 183, fourth section 184, fifth section 185, and sixth section 186. First section 181 may include patient specific information such as, for example, the patient's name, primary indication, whether the patient has a pace maker, the patients date of birth, gender and/or a patient ID. Second section 182 may include clinician information such as, for example, the overseeing physician, the name of the institute, the date of the analysis and/or a signature.

Third section 183 may include a plot of the ECG data. In FIG. 15A, section 183 includes a heart rate density plot similar to the one shown in FIG. 12. The window of time shown may be a default time or may be a user defined time window. Like the heart rate density plot in FIG. 12, a certain label may be selected to indicate the occurrence of an abnormality on the density plot. The time window is usually selected according to the relevant episodes and/or events. It is understood, however, that other plots may be included in the report such as an R-R plot.

Fourth section 184 may include metrics from the cardiac signal recording. For example, fourth section 184 may include the duration of the recording, the maximum, minimum and average heart rate, premature supraventricular complexes and any patient-triggered events, and/or any other metrics concerning the cardiac signal. Fifth section 185 may include information corresponding to any episodes detected. For example, fifth section 185 may include pause information (count and/or longest R-R interval), atrioventricular block information, atrial fibrillation/flutter information, ventricular tachycardia information, other supraventricular tachycardia information, and/or any other information concerning any episodes or abnormalities. Sixth section 186 may include results information such as, for example, a summary of the episodes and/or abnormalities, a diagnosis, and/or any other information analyzed, aggregated, computed, determined, identified, or otherwise detected from the cardiac signal. For example, sixth section 186 may identify a sinus rhythm with paroxysmal atrial fibrillation.

Figure 15B:
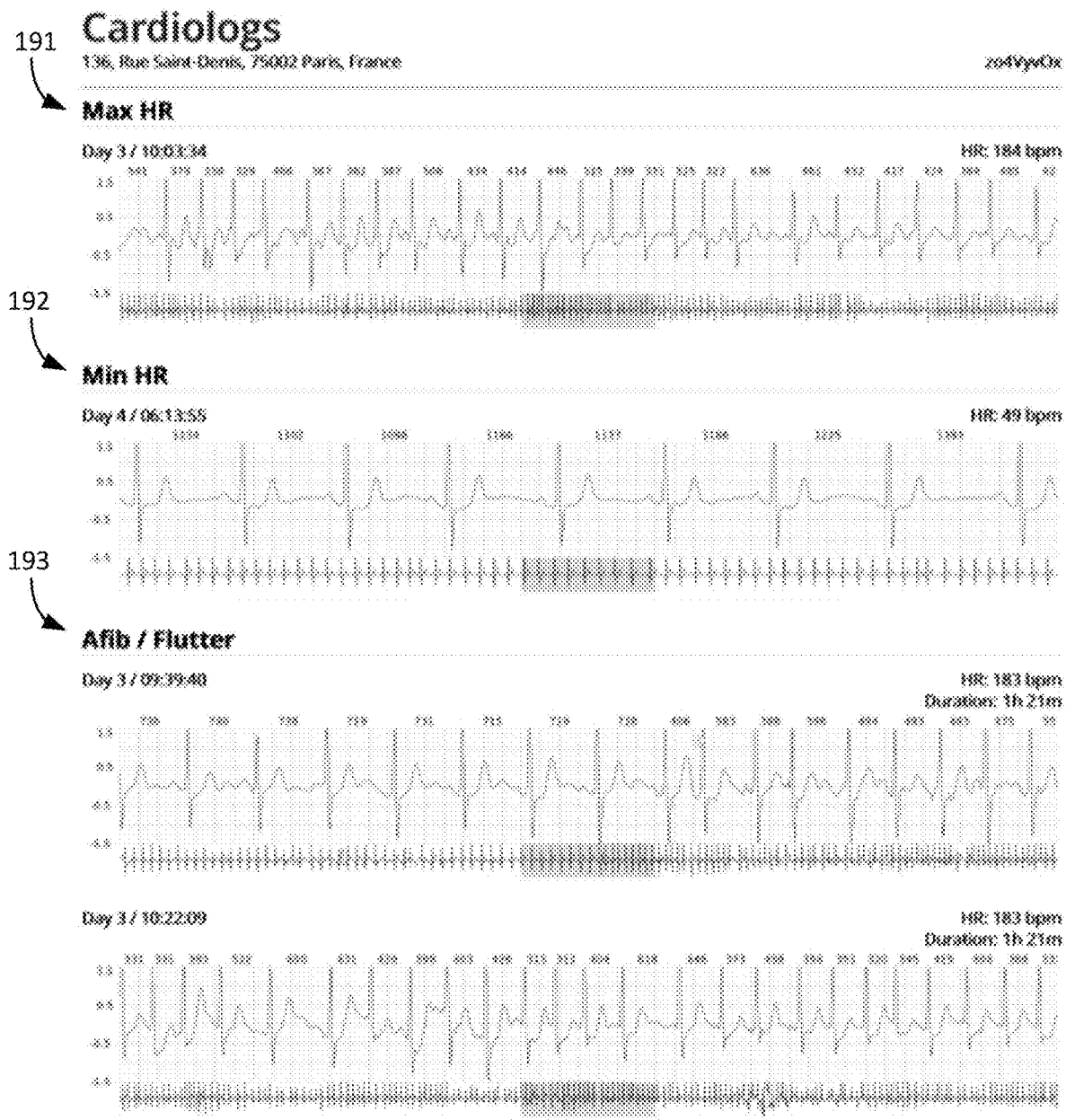
Figure 15C:
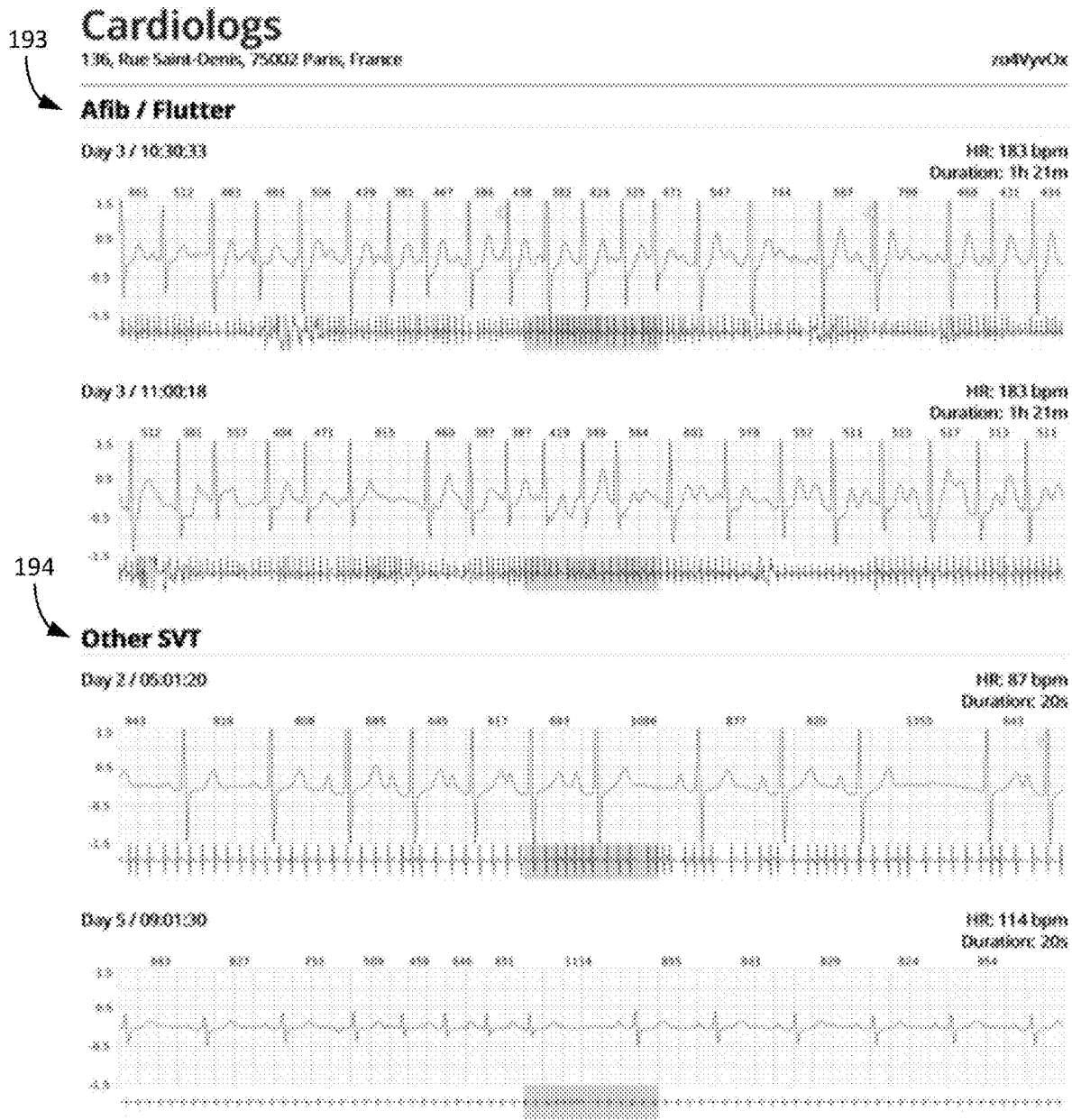
Figure 15D:
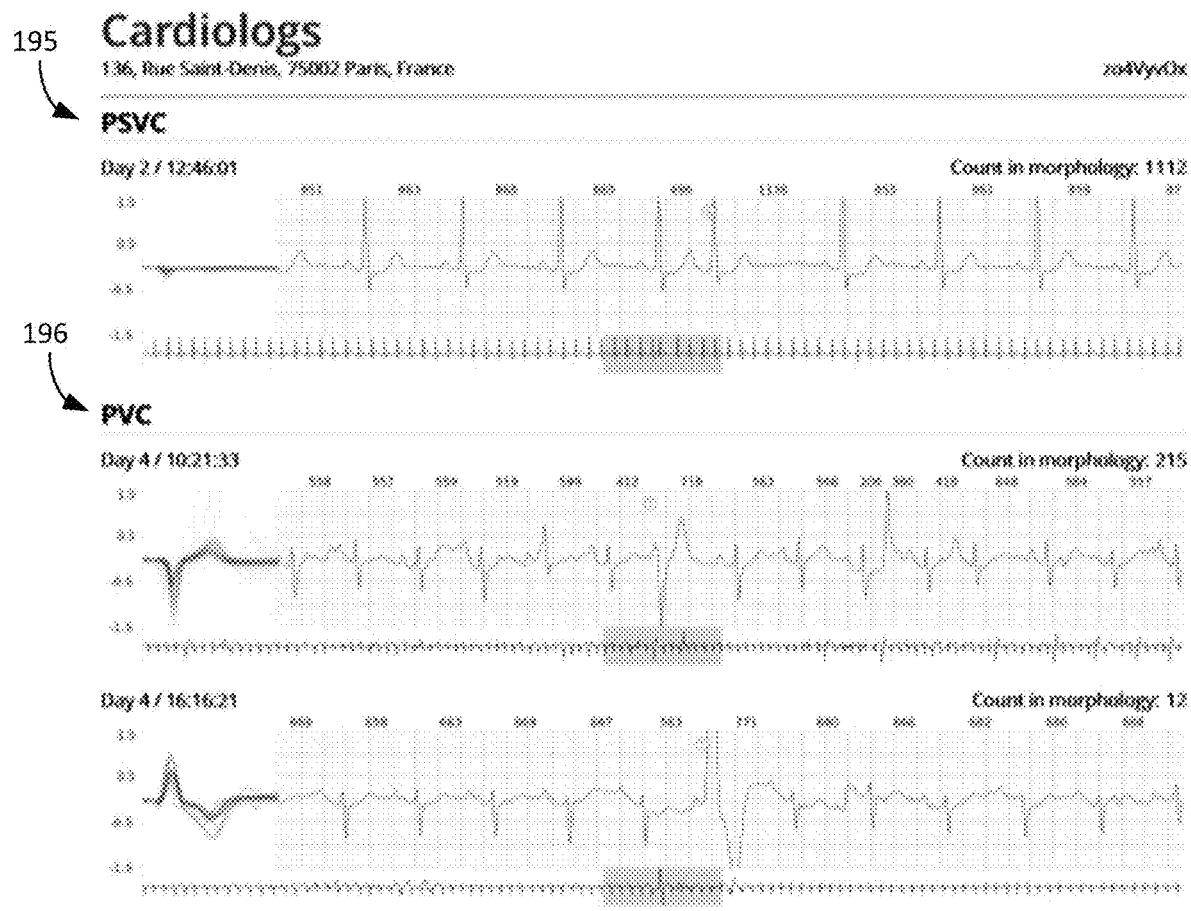

FIG. 15B-D illustrates the second, third and fourth pages of an exemplary report. As is shown in FIG. 15B-D, the report may further include ECG strips previously selected by the user, or selected under default settings. For example, a user may select Max HR strip 191, Min HR strip 192, Afib/Flutter strips 193, other SVT strips 194, PSVC strip 195, and PVC strip 196. Max HR strip 191 may be an ECG strip indicating the maximum heart rate during a given cardiac signal recording. Similarly, Min HR strip 191 may be an ECG strip indicating the minimum heart rate during a given cardiac signal recording. Afib/Flutter strips 193 may be ECG strips indicating each episode of atrial fibrillation/flutter. Other SVT strip 194 may be ECG strips indicating each episode of supraventricular tachycardia. PSVC strip 195 may be an ECG strip indicating an episode of premature supraventricular complex. PVC strip 197 may be ECG strips indicating episodes of premature ventricular complex. ECG strips may be displayed with the related relevant associated metrics and comments as added by the user. It is understood that the report shown in FIGS. 15A-B is merely exemplary and that the report generated at step 68 may have a different structure or configuration and/or may include different ECG and patient related information contemplated herein.

It should be understood that any of the operations described herein above may be implemented at least in part as computer-readable instructions stored on a computer-readable memory. Upon execution of the computer-readable instructions by a processor, the computer-readable instructions may cause a node to perform the operations. It will of course be understood that the embodiments described herein are illustrative, and components may be arranged, substituted, combined, and designed in a wide variety of different configurations, all of which are contemplated and fall within the scope of this disclosure.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims.

What is claimed is:

1. A system for analyzing electrocardiogram (ECG) data of a patient, the system comprising instructions stored on at least one server, the instructions configured to, when executed, cause the at least one server to:
    obtain a set of patient ECG data corresponding to a patient, the set of patient ECG data generated over a plurality of time points as sampled by a sensing device;
    process at least a portion of the set of patient ECG data using an algorithm to determine a presence of one or more abnormalities, conditions, or descriptors corresponding to a cardiac event associated with the set of patient ECG data, the algorithm trained using a plurality of sets of ECG data different from the set of patient ECG data;
    generate information, based on the processing, to indicate the presence of the one or more abnormalities, conditions, or descriptors corresponding to a cardiac event associated with the set of patient ECG data; and
    send the information corresponding to the presence of the one or more abnormalities, conditions, or descriptors determined for the set of patient ECG data for display.

2. The system of claim 1, wherein the instructions stored on the at least one server are further configured to cause the at least one server to cause a device to display a heart rate density plot based on the set of patient ECG data, the heart rate density plot representing a density of heart rates of the patient as a function of time.

3. The system of claim 2, wherein the heart rate density plot visually indicates the one or more abnormalities, conditions, or descriptors determined for the set of patient ECG data.

4. The system of claim 2, wherein the instructions stored on the at least one server are further configured to cause the at least one server to generate the heart rate density plot to permit zoom in and zoom out interaction on the heart rate density plot.

5. The system of claim 2, wherein the instructions stored on the at least one server are further configured to cause the at least one server to generate the heart rate density plot arranged with respect to a time axis and to permit navigating the heart rate density plot with respect to the time axis.

6. The system of claim 5, wherein the instructions stored on the at least one server are further configured to cause the at least one server to generate an ECG strip, wherein the time axis includes a cursor and a position of the cursor on the time axis of the heart rate density plot corresponds to a time window of the ECG strip.

7. The system of claim 5, wherein the instructions stored on the at least one server are further configured to (i) generate one or more label buttons corresponding to the heart rate density plot and (ii) cause the heart rate density plot to visually indicate the presence of one or more abnormalities, conditions, or descriptors when the one or more label buttons are engaged.

8. The system of claim 1, wherein the instructions stored on the at least one server are further configured to cause the at least one server to generate a report including at least the information corresponding to the presence of the one or more abnormalities, conditions, or descriptors determined for the set of patient ECG data.

9. The system of claim 8, wherein the report includes at least one heart rate density plot representing a density of heart rates of the patient as a function of time.

10. The system of claim 9, wherein the report visually indicates the presence of the one or more abnormalities, conditions, or descriptors in the at least one heart rate density plot.

11. The system of claim 1, wherein the instructions stored on the at least one server are further configured to cause the at least one server to pre-process the set of patient ECG data prior to processing the at least a portion of the set of patient ECG data using the algorithm, and wherein pre-processing the set of patient ECG data comprises removing noise from the set of patient ECG data or expressing the set of patient ECG data at a predetermined baseline frequency or both.

12. The system of claim 1, wherein processing the at least a portion of the set of patient ECG data using the algorithm comprises using at least one algorithm to apply the at least a portion of the set of patient ECG data to a first neural network.

13. The system of claim 1, wherein the algorithm utilizes machine learning to process the at least a portion of the set of patient ECG data and generate the information.

14. The system of claim 1, wherein the instructions stored on the at least one server cause the at least one server to process the at least a portion of the set of patient ECG data using the algorithm to determine a likelihood of the presence of one or more abnormalities, conditions, or descriptors corresponding to a cardiac event associated with the set of patient ECG data.

15. The system of claim 14, wherein the instructions stored on the at least one server, are further configured to cause the at least one server to compare the likelihood of a presence of one or more abnormalities, conditions, or descriptors to a threshold value, and wherein the information corresponding to the presence of the one or more abnormalities, conditions, or descriptors determined for the set of patient ECG data is sent for display if the likelihood of a presence of one or more abnormalities, conditions, or descriptors exceeds the threshold value.

16. The system of claim 1, wherein the instructions stored on the at least one server cause the at least one server to generate information indicating the presence of multiple abnormalities, conditions, or descriptors corresponding to multiple cardiac events associated with the set of patient ECG data.

17. A computerized method for analyzing electrocardiogram (ECG) data of a patient, the computerized method comprising:
obtaining a set of patient ECG data corresponding to a patient, the set of patient ECG data generated over a plurality of time points as sampled by a sensing device;
processing at least a portion of the set of patient ECG data using an algorithm to determine a presence of one or more abnormalities, conditions, or descriptors corresponding to a cardiac event associated with the set of patient ECG data, the algorithm trained using a plurality of sets of ECG data different from the set of patient ECG data;
generating information, based on the processing, to indicate the presence of the one or more abnormalities, conditions, or descriptors corresponding to a cardiac event associated with the set of patient ECG data; and
sending the information corresponding to the presence of the one or more abnormalities, conditions, or descriptors determined for the set of patient ECG data for display.

18. The computerized method of claim 17, further comprising causing a device to display a heart rate density plot based on the set of patient ECG data, the heart rate density plot representing a density of heart rates of the patient as a function of time.

19. The computerized method of claim 18, wherein the heart rate density plot visually indicates the one or more abnormalities, conditions, or descriptors determined for the set of patient ECG data.

20. The computerized method of claim 17, further comprising generating a report including at least the information corresponding to the presence of the one or more abnormalities, conditions, or descriptors determined for the set of patient ECG data.

21. The computerized method of claim 20, wherein the report includes at least one heart rate density plot representing a density of heart rates of the patient as a function of time.

22. The computerized method of claim 17, wherein all of the set of patient ECG data is processed by at least one server.

23. The computerized method of claim 17, wherein the one or more abnormalities, conditions, or descriptors corresponding to a cardiac event comprise atrial fibrillation associated with the set of patient ECG data.

24. The computerized method of claim 17, further comprising pre-processing the set of patient ECG data prior to processing the at least a portion of the set of patient ECG data using the algorithm, and wherein pre-processing the set of patient ECG data comprises removing noise from the set of patient ECG data or expressing the set of patient ECG data at a predetermined baseline frequency or both.

25. The computerized method of claim 17, wherein processing the at least a portion of the set of patient ECG data using the algorithm comprises using at least one algorithm to apply the at least a portion of the set of patient ECG data to a first neural network.

26. The computerized method of claim 25, wherein processing the at least a portion of the set of patient ECG data using the algorithm further comprises using the at least one algorithm to apply the at least a portion of the set of patient ECG data to one or more additional neural networks.

27. The computerized method of claim 17, wherein the algorithm utilizes machine learning to process the at least a portion of the set of patient ECG data and generate the information.

28. The computerized method of claim 17, further comprising generating information indicating the presence of multiple abnormalities, conditions, or descriptors corresponding to multiple cardiac events associated with the set of patient ECG data.

29. A non-transitory computer-readable memory medium configured to store instructions thereon that when loaded by at least one processor cause the at least one processor to:
  obtain a set of patient ECG data corresponding to a patient, the set of patient ECG data generated over a plurality of time points as sampled by a sensing device;
  process at least a portion of the set of patient ECG data using an algorithm to determine a presence of one or more abnormalities, conditions, or descriptors corresponding to a cardiac event associated with the set of patient ECG data, the algorithm trained using a plurality of sets of ECG data different from the set of patient ECG data;
  generate information, based on the processing, to indicate the presence of the one or more abnormalities, conditions, or descriptors corresponding to a cardiac event associated with the set of patient ECG data; and
  send the information corresponding to the presence of the one or more abnormalities, conditions, or descriptors determined for the set of patient ECG data for display.

30. The non-transitory computer-readable memory medium of claim 29, wherein the instructions loaded by the at least one processor further cause the at least one processor to cause a device to display a heart rate density plot based on the set of patient ECG data, the heart rate density plot representing a density of heart rates of the patient as a function of time.

* * * * *